US011730865B2

(12) United States Patent
Sawhney et al.

(10) Patent No.: US 11,730,865 B2
(45) Date of Patent: Aug. 22, 2023

(54) EMBOLIC COMPOSITIONS AND METHODS

(71) Applicant: Incept, LLC, Lexington, MA (US)

(72) Inventors: Amarpreet S. Sawhney, Lexington, MA (US); Hans Claesson, Lexington, MA (US); Raymond Lareau, Westford, MA (US); Douglas Billings, Wellesley, MA (US)

(73) Assignee: Incept, LLC, Lexington, MA (US)

( * ) Notice: Subject to any disclaimer, the term of this patent is extended or adjusted under 35 U.S.C. 154(b) by 1105 days.

(21) Appl. No.: 16/409,633

(22) Filed: May 10, 2019

(65) Prior Publication Data

US 2019/0351107 A1 Nov. 21, 2019

Related U.S. Application Data

(60) Provisional application No. 62/671,836, filed on May 15, 2018.

(51) Int. Cl.
| | | |
|---|---|---|
| *A61L 31/04* | (2006.01) | |
| *A61M 25/00* | (2006.01) | |
| *A61L 31/14* | (2006.01) | |
| *A61B 17/12* | (2006.01) | |
| *A61L 24/00* | (2006.01) | |

(Continued)

(52) U.S. Cl.
CPC ...... *A61L 31/048* (2013.01); *A61B 17/12113* (2013.01); *A61B 17/12186* (2013.01); *A61B 17/12195* (2013.01); *A61L 24/0031* (2013.01); *A61L 24/02* (2013.01); *A61L 24/06* (2013.01); *A61L 31/145* (2013.01); *A61M 25/0026* (2013.01); *C08F 120/28* (2013.01); *A61L 2300/44* (2013.01); *A61L 2300/80* (2013.01); *A61L 2400/06* (2013.01);
(Continued)

(58) Field of Classification Search
None
See application file for complete search history.

(56) References Cited

U.S. PATENT DOCUMENTS

| | | | | |
|---|---|---|---|---|
| 6,676,971 B2 * | 1/2004 | Goupil | ................. | A61L 29/085 424/501 |
| 2001/0036451 A1 | 11/2001 | Goupil et al. | | |

(Continued)

FOREIGN PATENT DOCUMENTS

| | | |
|---|---|---|
| CN | 101537210 A | 9/2009 |
| JP | 2002-522174 A | 7/2002 |

(Continued)

OTHER PUBLICATIONS

Lee et al., "Retained Microcatheter after Onyx Embolization of Intracranial Arteriovenous Malformation". J Korean Neurosurg Soc. Jun. 2012; 51(6): 374-376.

(Continued)

*Primary Examiner* — Tae H Yoon
(74) *Attorney, Agent, or Firm* — Christensen, Fonder, Dardi; Peter S. Dardi; Robert E. Holthus

(57) ABSTRACT

An embolization system and methods for controlling solidification of embolic compositions comprising a first and a second embolic component that react with each other in vivo at a target site to form an embolic material, with the embolic components being dilutable in physiological fluids so that they do not form an embolic composition at a site that is not desired.

17 Claims, 17 Drawing Sheets

(51) Int. Cl.
  *A61L 24/02* (2006.01)
  *A61L 24/06* (2006.01)
  *C08F 120/28* (2006.01)
  *C08F 4/38* (2006.01)

(52) U.S. Cl.
  CPC .. *A61L 2430/36* (2013.01); *A61M 2025/0039* (2013.01); *C08F 4/38* (2013.01)

(56) References Cited

U.S. PATENT DOCUMENTS

| | | |
|---|---|---|
| 2005/0133046 A1 | 6/2005 | Becker et al. |
| 2005/0271727 A1 | 12/2005 | Yao |
| 2007/0282366 A1 | 12/2007 | Khosravi et al. |
| 2009/0017097 A1 | 1/2009 | Sawhney et al. |
| 2010/0063472 A1 | 3/2010 | Becker et al. |
| 2011/0142936 A1 | 6/2011 | Campbell et al. |
| 2012/0071865 A1 | 3/2012 | Jarrett et al. |
| 2012/0114589 A1 | 5/2012 | Rolfes-Meyering et al. |

FOREIGN PATENT DOCUMENTS

| | | |
|---|---|---|
| JP | 2003-525683 A | 9/2003 |
| JP | 2003-527402 A | 9/2003 |
| WO | 2001068720 | 9/2001 |
| WO | 2010047799 | 4/2010 |

OTHER PUBLICATIONS

Qureshi et al, "Occurrence and Management Strategies for Catheter Entrapment with Onyx Liquid Embolization". J. Vasc Interv Neurol. Jul. 2015; 8(3): 37-41.

Debrun et al., "Glued Catheters during Embolisation of Brain AVMs with Acrylic Glue". Interv Neuroradiol. Mar. 30, 1997; 3(1):13-19. Epub May 15, 2001.

International Search Report and Written Opinion from corresponding PCT application No. PCT/US2019/031869, dated Aug. 13, 2019, 11 pages.

First Office Action from corresponding Chinese Patent Application No. 2019800323808, 13 pages, dated Nov. 19, 2021.

Office Action from corresponding Japanese Patent Application No. 2020-564239, 10 pages, dated Apr. 4, 2023.

\* cited by examiner

EMBOLIC COMPOSITIONS AND METHODS

CROSS REFERENCE TO RELATED APPLICATIONS

This patent application claims priority to U.S. Provisional Application No. 62/671,836 filed May 15, 2018, which is hereby incorporated by reference herein for all purposes.

TECHNICAL FIELD

The technical field relates to methods of embolizing target tissue, and devices and compositions for the same, including coaxial catheter systems that deliver embolic components in a vasculature to react in situ to form an embolization material.

BACKGROUND

Embolization involves blocking blood circulation or other fluids by the introduction of embolic components. Embolization uses include treatment of aneurysms, a hemostatic treatment for bleeding, or deliberately blocking blood vessels of certain kinds of tumors. In general, a medical services provider uses imaging guidance to insert a catheter into a primary lumen, such as an artery, and advances it to a blood vessel leading to the target site, such as an aneurysm, tumor or other target area as a lacerated vessel. Mechanical devices or materials that form a blockage are then injected.

SUMMARY OF PREFERRED EMBODIMENTS

An embodiment of the invention is a method of embolization comprising delivering a first liquid comprising a co-initiator through a first catheter lumen to a target lumen and delivering a second liquid that comprises an initiator through a second catheter lumen to the target lumen, with at least one of the first liquid and the second liquid further comprising at least one water soluble polymer that comprises a plurality of functional groups that each comprise an unsaturated hydrocarbon. The co-initiator and the initiator react to form a radical initiator which polymerizes the unsaturated moieties of the at least one water soluble polymer to form an embolization material in the target lumen upon mixing. The embolization material is designed so that it does not form in vivo when it is diluted beyond a predetermined amount by blood or other fluids. At the same time, however, the embolization material forms effectively at the intended site of use. In one embodiment, the components are chosen so that a predetermined percentage of a dilution of a mixture of the first liquid and the second liquid prevents formation of the embolization material or provides a substantial delay, e.g., more than 120 seconds, in gel formation as measured by a failure to form the embolization material in an in vitro gel time test. An example of a predetermined dilution amount is a value in a range from 100% v/v to 400% v/v.

Another embodiment of the invention is an embolization system for controlling solidification in vivo of embolic compositions comprising one or more of: a first fluid supply containing a first liquid, a second fluid supply containing a second liquid, a water soluble polymer that comprises at least two functional groups that comprise an unsaturated hydrocarbon, an initiator, and a co-initiator, with the initiator being disposed in one of the first liquid and the second liquid and the co-initiator being disposed in the other of the first liquid and the second liquid, with the water soluble polymer being disposed in at least one of the first liquid and the second liquid. A mixture of the first liquid and the second liquid provides for reaction of the initiator and the co-initiator to form a radical initiator for a free radical polymerization of the functional groups to covalently crosslink the water soluble polymer to form an embolization material. The components may be chosen so that a predetermined dilution prevents or significantly delays formation of the embolic material. For instance, a 300% v/v or a 400% v/v dilution of a 1:1 v/v mixture of the first liquid and the second liquid prevents the formation of the embolization material as measured by a failure to form the embolization material within 120 seconds as measured with an in vitro gel time test. The system may include one or more catheters and/or catheter adaptors.

DETAILED DESCRIPTION

Figure 1:
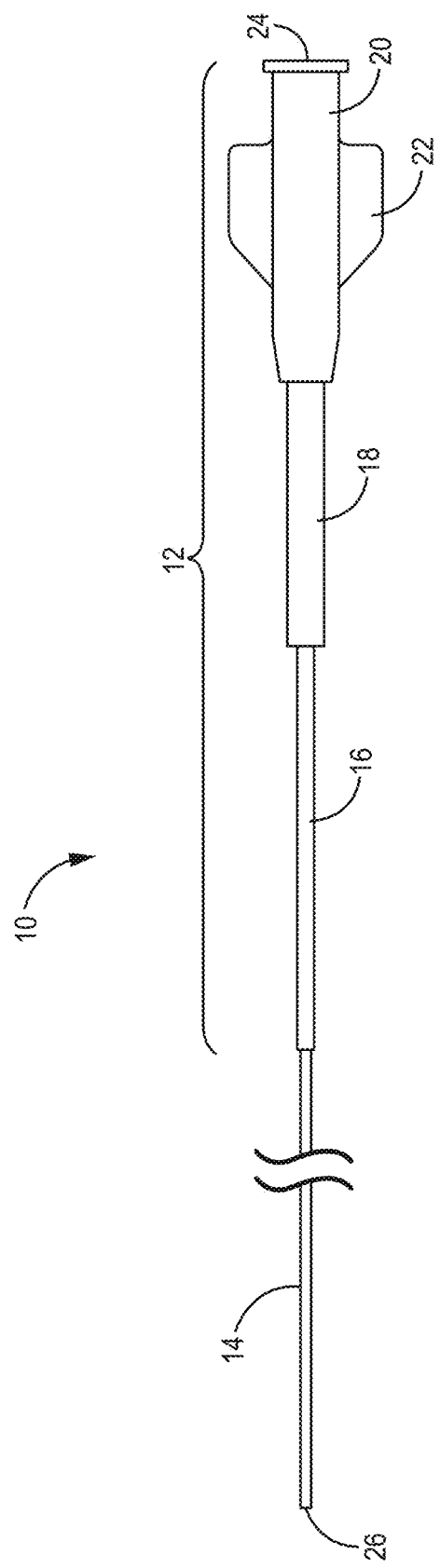
FIG. 1 depicts an embodiment of an inner catheter for use in a coaxial catheter system.

Certain embodiments of the invention are directed to delivery of embolic components that can chemically react to form embolic materials despite dilution effects caused by flowing blood or other factors. Hydrogels are preferred embolic materials. The embolic components are deliverable through a coaxial catheter system. The catheter distal ends are positioned in a vasculature and release embolic components that form the embolic material distal to the catheters at a target site in the vasculature. The embolic components are released from separate catheter lumens and mix to chemically react with each other to form the hydrogel or other embolic material. It was determined that the embolic components could be chosen to form effective embolic materials despite dilutive effects of flowing blood and interference from blood and tissue proteins and biomolecules. On the other hand, it was further desired that the embolic materials be formed only at targeted sites. Embolic components and compositions were created so that they would minimize the risk to form embolic materials at locations that were not at the target site. One solution developed for preventing the embolic material from forming was to provide components that would fail to form the embolic material when they were diluted by a predetermined degree of dilution such as a percentage volume dilution. As can be appreciated by a person of skill in these arts, a goal of making an embolic material such as a hydrogel that forms an effective embolic material under dynamic dilutive conditions such as flowing blood is in opposition with a goal of making a hydrogel that fails to form an embolic material upon dilution at off-target locations.

One useful system is based on a hydrogel precursor having a plurality of free radical polymerizable groups that is mixed with an initiator and co-initiator. An embodiment of the hydrogel precursor is a water soluble polymer with a plurality of vinylic functional groups. The water soluble polymer combined with a co-initiator is referred to as a hydrogel precursor since, upon reaction, it forms a hydrogel and is part of the hydrogel matrix. The hydrogel is formed upon initiation of crosslinking of vinyl groups through a free radical polymerization reaction. The free radical initiators are created combining reagents consisting of a peroxide and a reductant. The peroxide may be referred to as an initiator and/or the reductant may be referred to as a co-initiator: the initiator and co-initiator cooperate to form a further initiator that may be referred to as a free radical initiator. Another system is based on a plurality of hydrogel precursors, with one of the precursors having a plurality of electrophilic groups and another of the precursors having a plurality of nucleophilic groups that are mixed together under a limiting condition wherein they do not react, for instance at a low pH. These precursors are used to form an embolic by combining them with a reagent that changes the pH or other limiting condition so that a reaction may take place. An embodiment a hydrogel precursor is a water soluble polymer with a plurality of the functional groups.

An embodiment of an embolization system for controlling solidification in vivo of embolic compositions has a first fluid supply containing a first liquid that comprises a water soluble polymer comprising a plurality of vinylic functional groups and a reductant (co-initiator), a second fluid supply containing a second liquid that comprises an initiator) in the form of a peroxide, a catheter adaptor connectable to the first fluid supply for delivery of the first liquid to a first catheter lumen and connectable to the second fluid supply for delivery of the second liquid to a second catheter lumen, wherein a 1:1 v/v mixture of the first liquid and the second liquid provides the free radical source for polymerization of the vinylic groups to covalently crosslink the water soluble polymer to form an embolization material, wherein a predetermined degree of dilution prevents formation of the embolic material in vivo. An in vitro gel time test is useful to assess dilution sensitivity of the embolic precursors. In one embodiment, a 400% v/v dilution of a 1:1 v/v mixture of the first liquid and the second liquid prevents formation of the embolization material as measured by a failure to form the embolization material within a time limit, e.g., of 0.3-30 minutes, according to in an in vitro gel time test. Alternatively, a different volume percentage dilution may be chosen, as described below.

The term embolization means a process or state in which a physiological lumen, blood vessel, organ, or other target tissue is obstructed by the lodgment of a material mass, which may be referred to as an embolus or embolic material. The term target tissue is broad and may be, for example, a blood vessel, organ, tumor, fibroid, cell mass, aneurysm, cancer, tumor, hypervascular tumor (cancerous or benign), aneurysm, aortic aneurysm, abdominal aortic aneurysm, peripheral aneurysm, hemostasis, vascular laceration, venous laceration, or tissue having a pathological condition. In the case where a target tissue is served by a blood vessel, embolization of the blood vessel that serves the target tissue causes the target tissue to be embolized, for example, embolization of blood vessels serving a tumor is said to be an embolization of the tumor. The embolization may take place in a target lumen, for instance a blood vessel, artery, vein, or other physiological lumen.

Delivery of Embolic Components with Catheter Systems, Coaxial and Multilumen Catheters Catheter systems with a plurality of lumens, preferably lumens that are slidably displaceable relative to each other, for instance coaxial catheters, are useful for delivery of the embolic components. Other catheters may be used, for instance, a single catheter with a plurality of lumens. Embodiments may include catheters or catheter systems with lumens that are displaceable relative to each other by an offset distance are useful.

Figure 2:
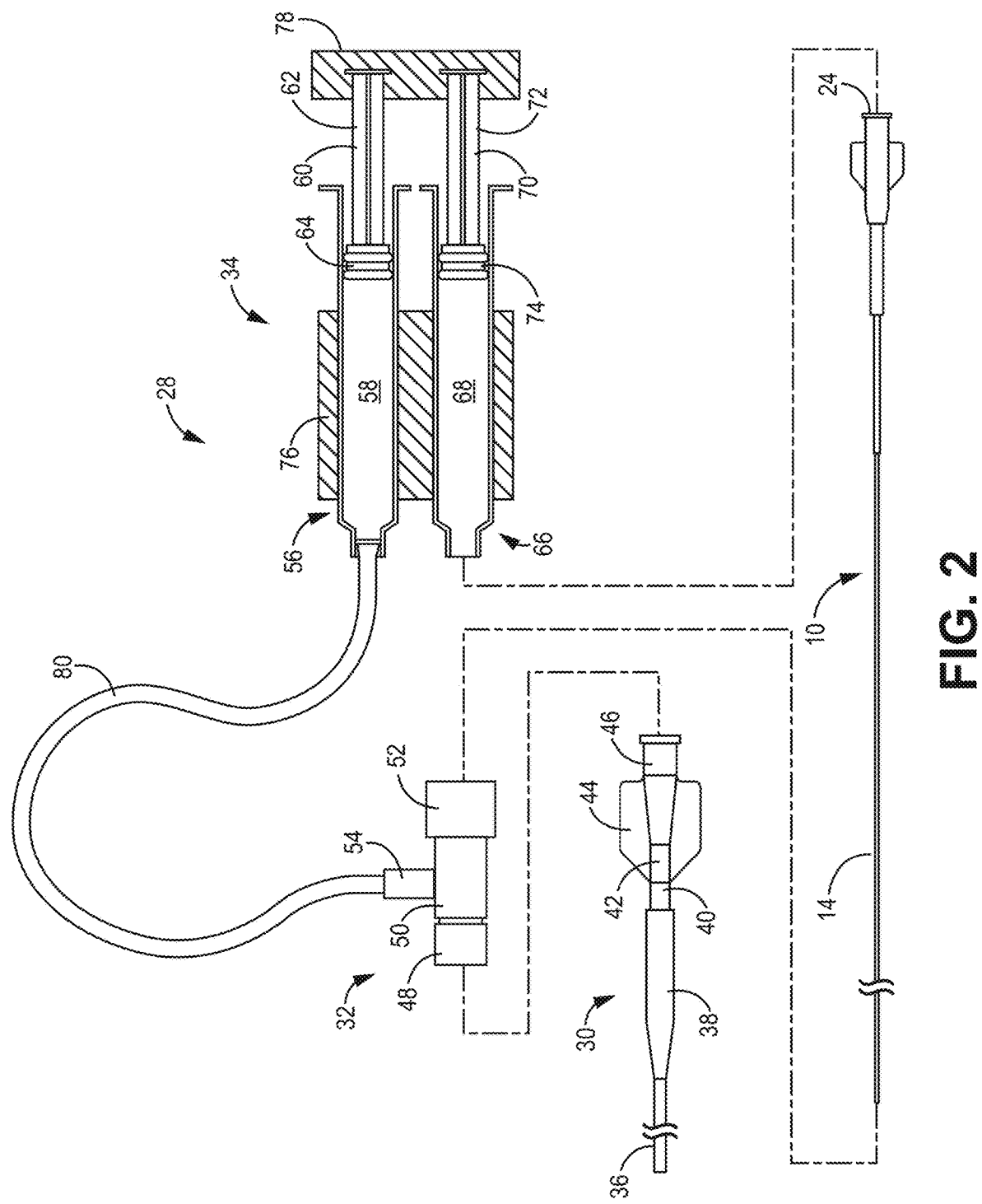
FIG. 2 is an exploded view of a coaxial catheter system that includes the inner catheter of FIG. 1.
Figure 3:
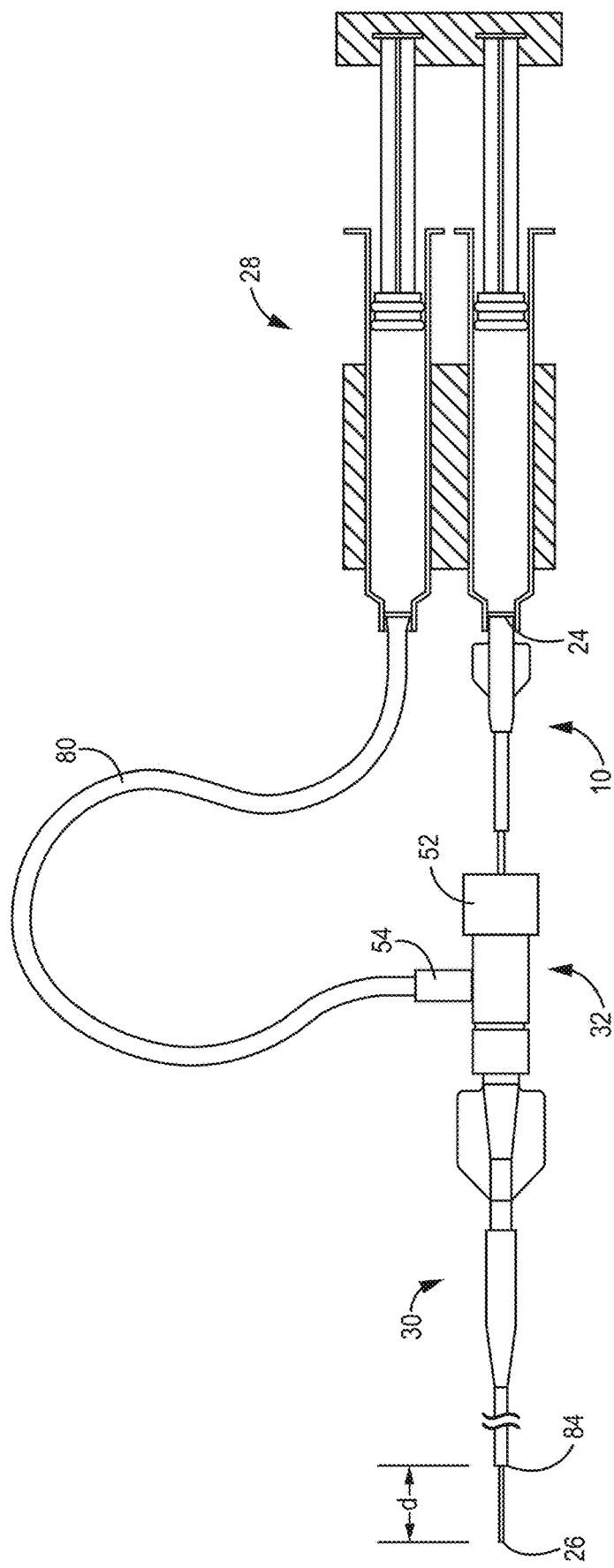
FIG. 3 is a plan view of the coaxial catheter system of FIG. 2, with the dual syringe assembly depicted in cross-sectional view.

FIGS. 1-3 depict an embodiment of a coaxial catheter system, with the catheters being displaceable relative to each other. FIG. 1 depicts small diameter catheter 10 having hub assembly 12 and shaft 14. Hub assembly 12 had intermediate portion 16, strain relief member 18, and hub 20 with hub wings 22 and proximal hub connecter 24. Shaft catheter 14, which may be used to provide the inner catheter in certain embodiments described below, has distal outlet tip 26. Artisans are familiar with these components, which may be custom made or obtained from commercial sources. Strain relief member 18 provides a transition from flexible shaft catheter 14 to hub 20. Intermediate portion 16 is optional and may be provided as a further strain relief member over shaft catheter 14 and/or as a portion of shaft catheter that has a large inner diameter (ID) and/or outer diameter (OD). FIG. 2 is an exploded view of coaxial catheter system 28 with inner catheter 10, outer catheter 30, coaxial catheter adaptor (Tuohy-Borst) 32, and dual syringe 34. Outer catheter 30 has outer catheter shaft 36, outer catheter strain relief member 38, distal hub connector 40, hub 42, hub wings 44, and proximal hub connector 46. Coaxial catheter adaptor 32 has distal connector 48, body 50, proximal connector 52, and side arm 54. Coaxial catheter adaptor adaptors such as the Tuohy-Borst adaptor have a sealing member (not shown) that provides a seal around catheters passed therethrough and side arm 54 provides fluid communication between the side arm and the annulus formed between inner catheter shaft 14 and outer catheter shaft 36. Dual syringe 34 has syringe 56 that has fluid supply (body) 58, plunger 60, plunger handle 62, and seal 64; syringe 66 that has fluid supply (body) 68, plunger 70, plunger handle 72, and seal 74; holder 76 holds syringes 56, 66; and end piece 78 joined to plungers 60, 70. Connector 80, depicted as a flexible tube, joins syringe 56 to side arm 54.

Outer catheter 30 is connected to coaxial catheter adaptor 32 through proximal hub connector 46 and distal connector 48. Inner catheter 10 passes through coaxial catheter adaptor 32 with inner catheter shaft 14 disposed inside outer catheter shaft 36. Side arm 54 is connected to syringe 56 through connector 80. Inner catheter 10 is connected to syringe 66 through proximal hub connector 24. When assembled as in FIG. 3, fluid supply 68 is in fluid communication with the lumen of inner catheter shaft 14 and fluid supply 58 is in fluid communication with the annulus formed between inner catheter shaft 14 and outer catheter shaft 36. Fluid supplies 58 and 68 contain liquids that comprise embolic components. Inner catheter distal tip 82 is slidable relative to outer catheter distal tip 84 and, as depicted, tip 26 may be extended distally relative to tip 84. In use, outer catheter shaft 36 may be introduced into a vasculature using known techniques and tip 84 positioned at a desired location. Coaxial catheter adaptor 32 is connected to outer catheter 30 and inner catheter shaft 14 is passed therethrough and positioned with tip 82 as desired. Dual syringe 28 is connected to side port 54 and hub connector 24. These embodiments are merely exemplary and other configurations may be used, for example an outer catheter with a hub to catheter connection with strain relief over the bond joint.

Figure 4A:
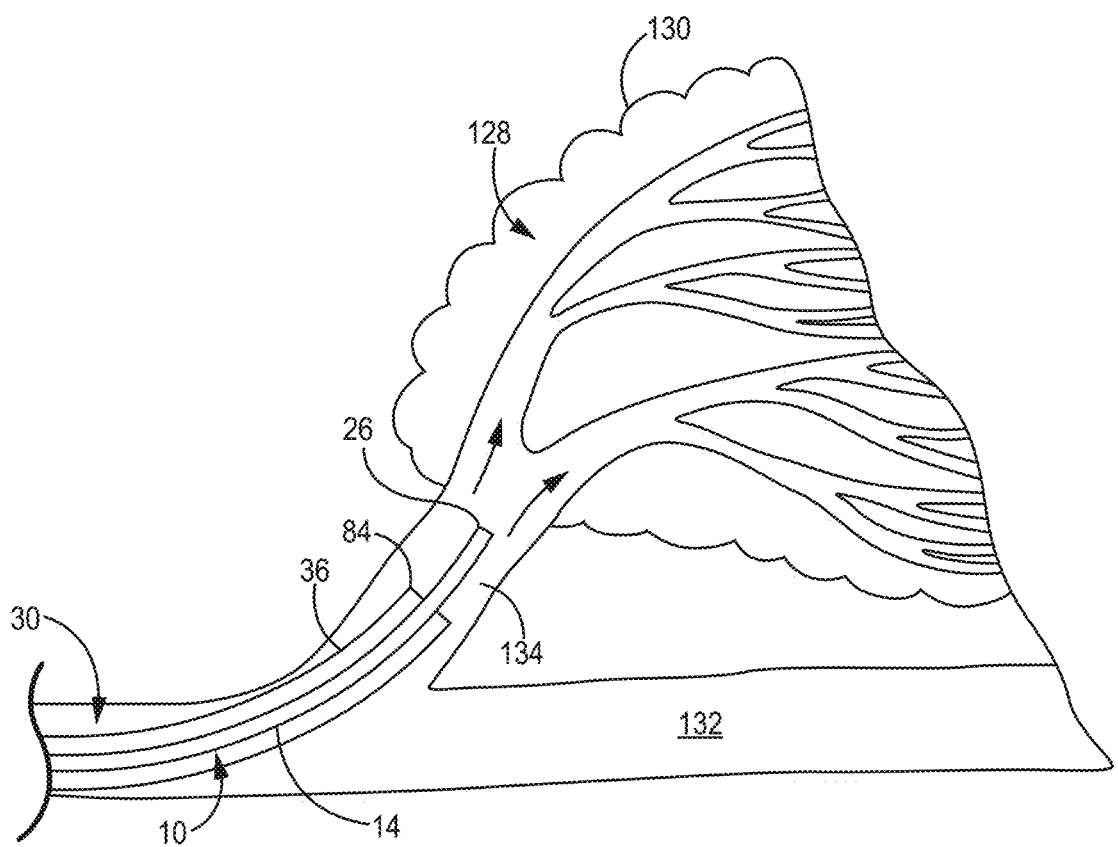
FIG. 4A depicts an embodiment of a use of the catheter system of FIG. 3, with the coaxial catheter in a deployed position.
Figure 4B:
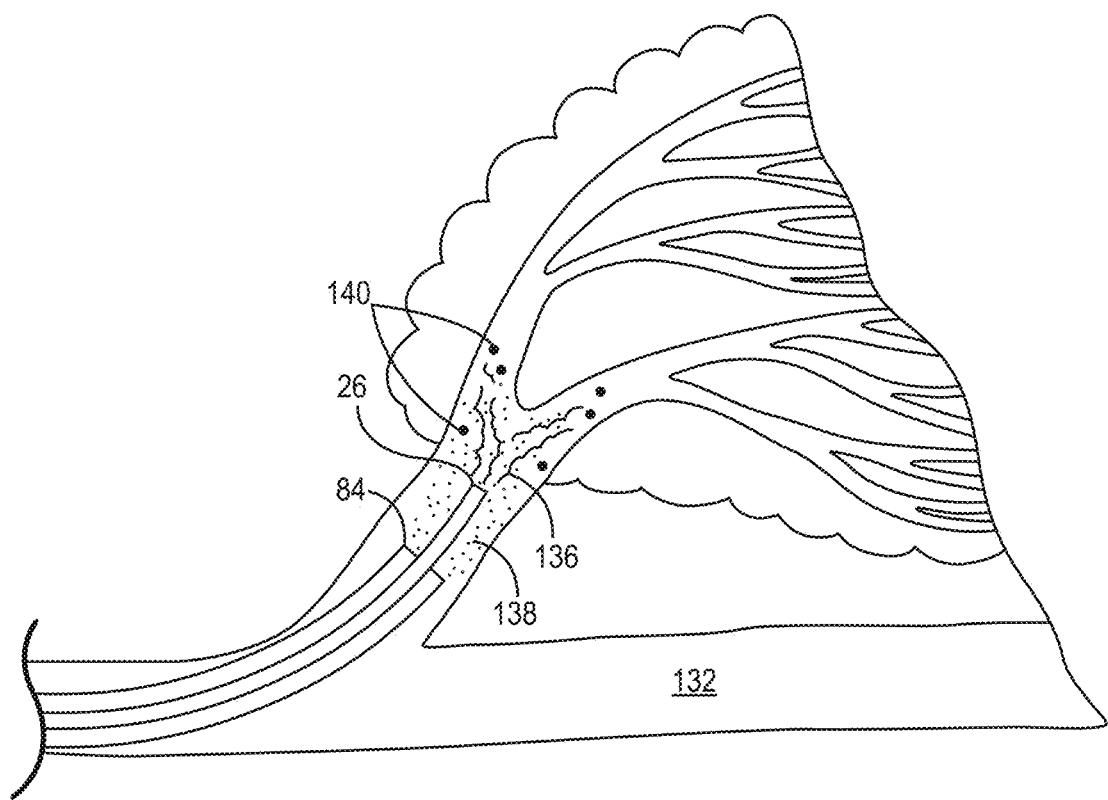
FIG. 4B depicts the catheter system of FIG. 4A releasing embolic components.
Figure 4C:
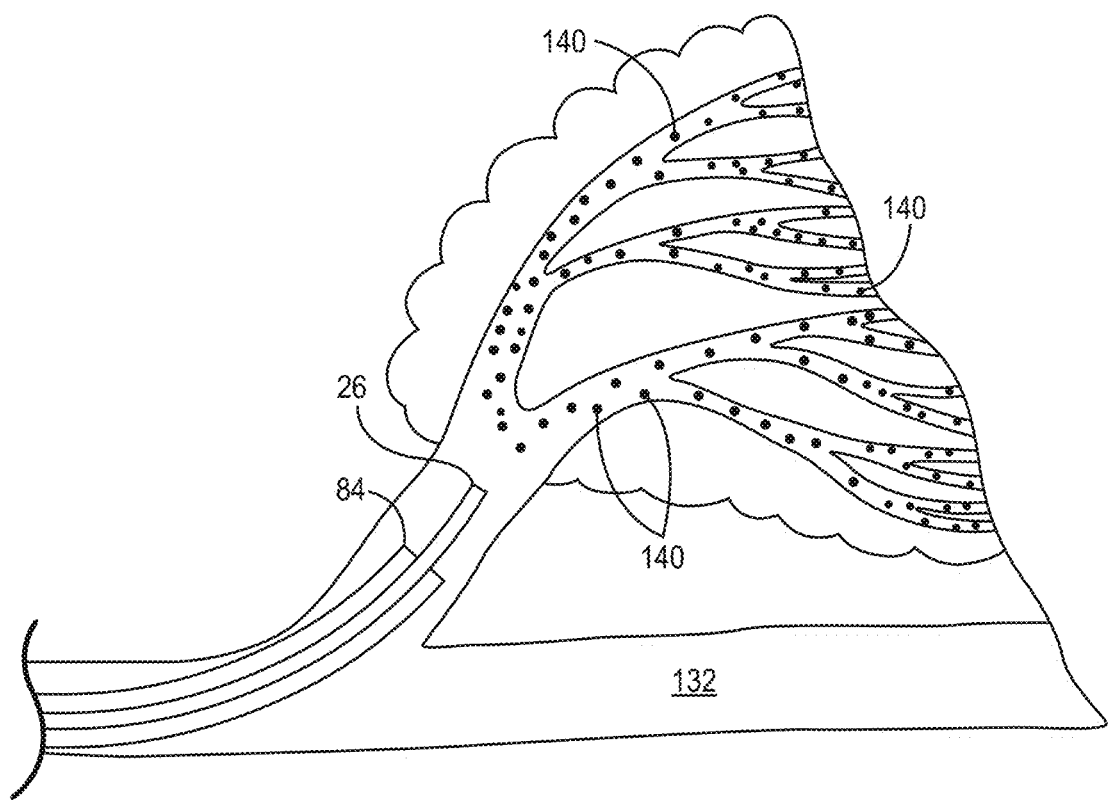
FIG. 4C depicts the catheter system of FIG. 4B after release of embolic components.
Figure 4D:
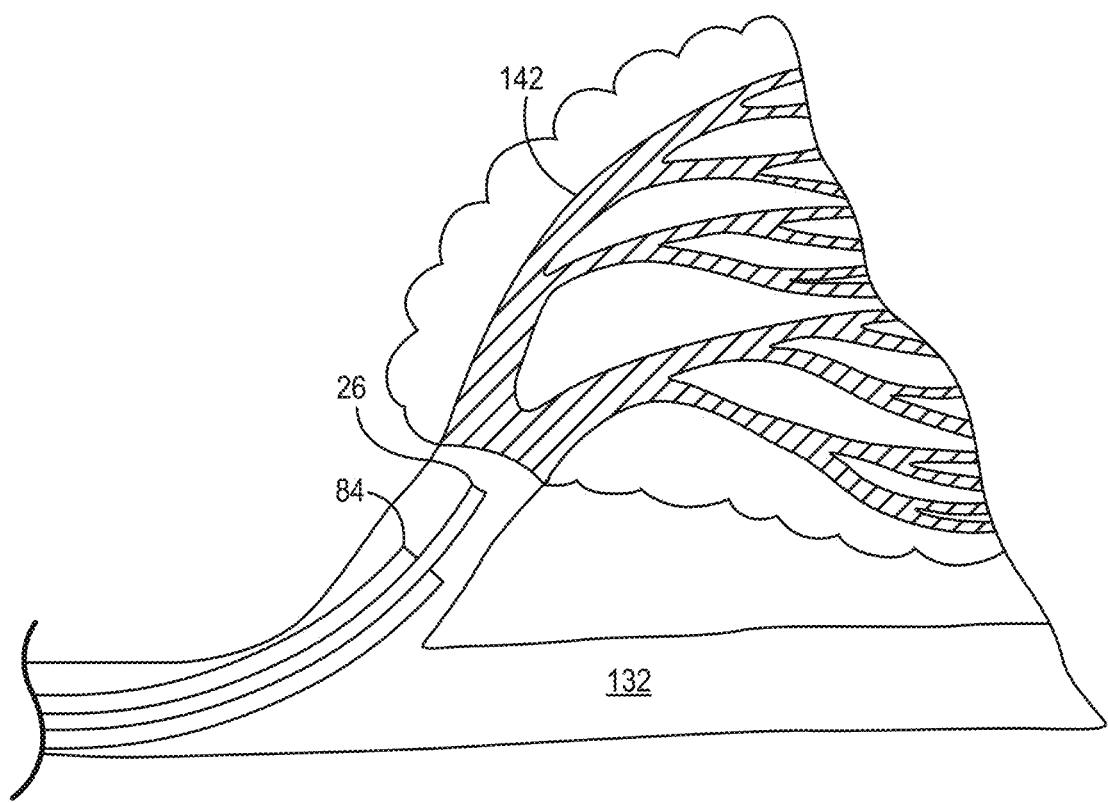
FIG. 4D depicts an embolic material in place after release of embolic components from the catheter system of FIG. 4C.

FIGS. 4A-4E depict a use of a coaxial catheter. The term coaxial is used broadly to encompass a system with one catheter that is disposed inside a lumen of another catheter, with the central axes of the inner catheter and the lumen being substantially parallel as limited by the disposition or movement of the inner catheter in the lumen. The coaxial inner catheter may be deployed in an off-center lumen or a central lumen. Surgical or minimally invasive access is obtained to an artery or vein using standard interventional technique enabling access and cannulation. A guide catheter and suitable imaging techniques may be used as helpful to locate distal tip 84 of outer catheter 30. In FIG. 4A, a portion of a vascular bed is depicted as vascular bed 128 having multiple branches in a tissue such as hypervascular tumor 130. The vascular vessel 132 is a vein or artery that is in communication with vascular bed 128. Distal tip 84 is located in vascular branch 134 and distal tip 26 of the inner catheter is passed through the outer catheter and located distal to catheter tip 84. The arrows indicate a direction of blood flow. FIG. 4B depicts a first liquid released from tip 26 that comprises embolic composition that contains a precursor 136. And tip 84 releases a liquid that comprises an embolic composition that includes an initiator 138 represented by small dots. A co-initiator such as a reductant may further be included in the system, as in the case where redox reagents are used with unsaturated functional groups.

Without being bound to a particular theory, when released into flowing blood or other flowing fluid, the embolic compositions can be provided to promote formation of domains 140 that are conceptually depicted in the Drawings. Embolic domains 140, FIG. 4C, move downstream in vascular bed 128 and flow through multiple branch points until they react and reach blood vessels that are too small to pass domains 140. The embolic domains react within and to each other to accumulate and block blood flow and embolize vascular bed 128. Dissection of hydrogels from organs and tissues using methods described in the Examples has generally revealed that the domains provide for formation continuous structures. It is also believed that the embolic compositions, when they do not completely fill a lumen, swell after placement to provide essentially complete filling of the. Channeling through the embolic material has not been observed: blood flow was completely blocked. The embolic compositions were observed to be securely located after placement, with a mechanical apposition to the blood vessels or other locations: the local changes in shape, in direction, and in dimensions prevented movement of the embolic materials after their placement.

Figure 4E:
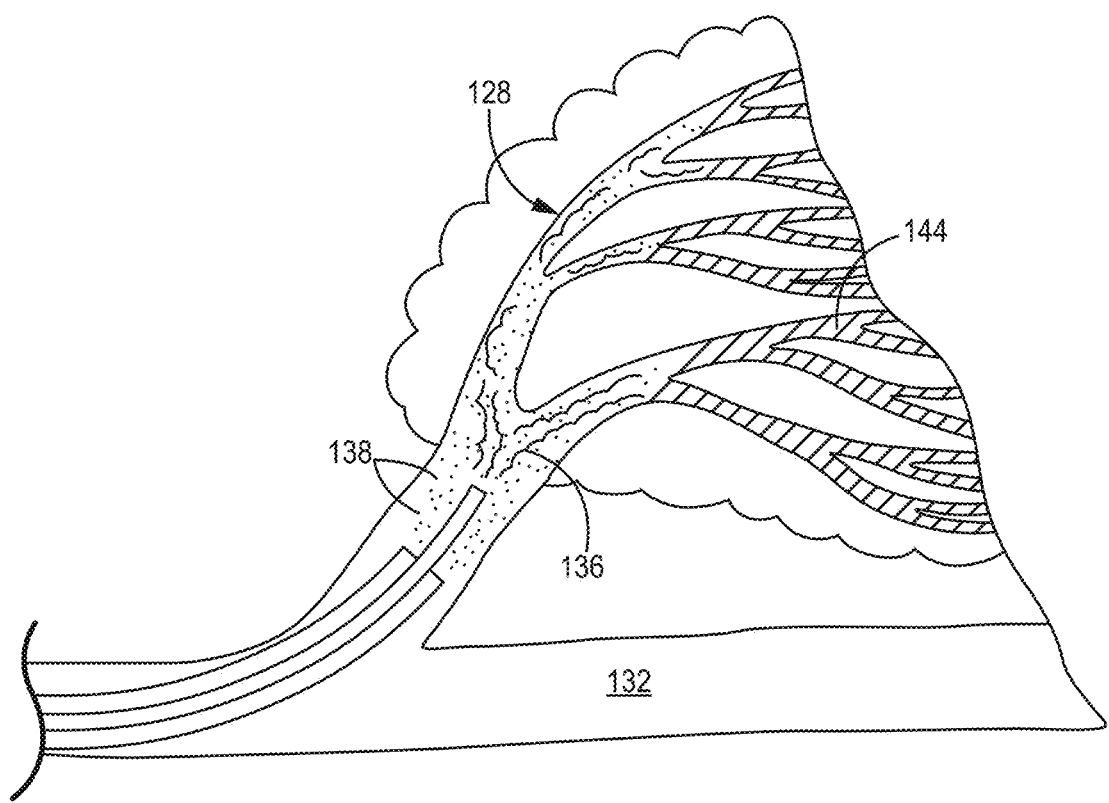
FIG. 4E depicts an alternative embodiment of a use of the catheter system of FIG. 3, with the coaxial catheter in a deployed position and releasing embolic components.

An alternative method of embolization is depicted in FIG. 4E wherein precursor 136 and initiator 138 provide a longer reaction time so that they penetrate into various branches of vascular bed 128 before reacting to form embolic material 144.

Figure 5:
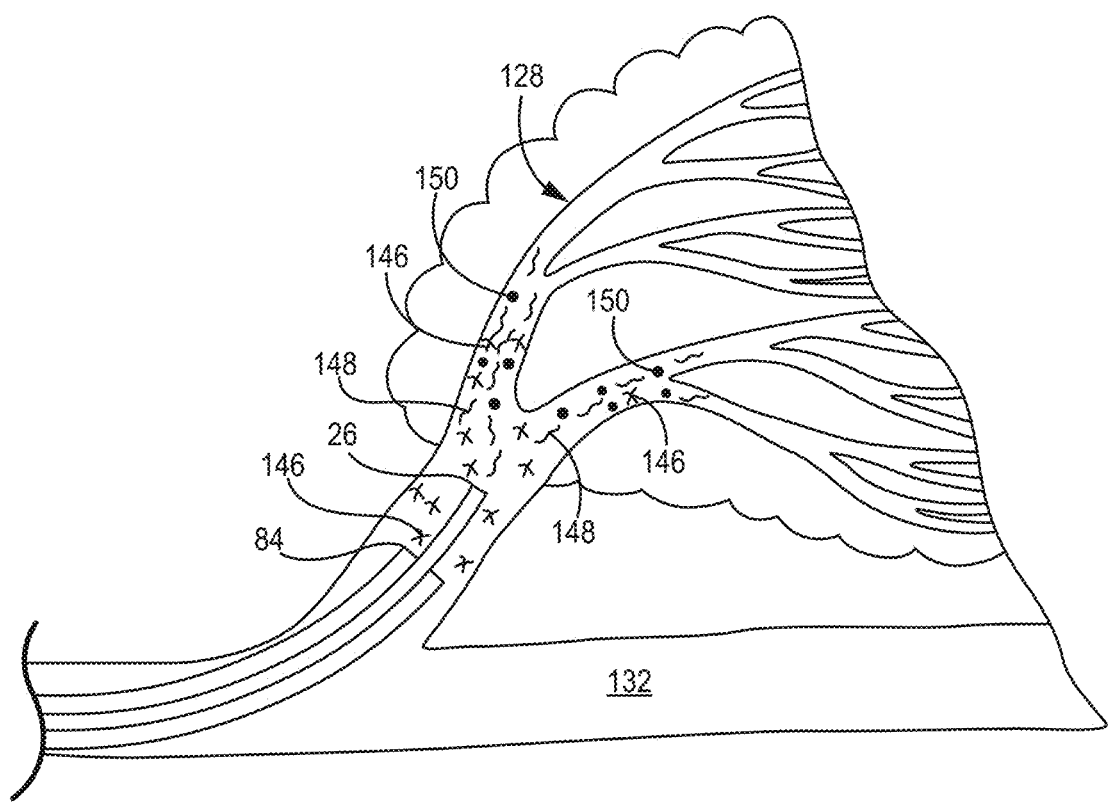
FIG. 5 depicts an alternative embodiment of a use of the catheter system of FIG. 3, with the coaxial catheter in a deployed position and releasing embolic components.
Figure 6A:
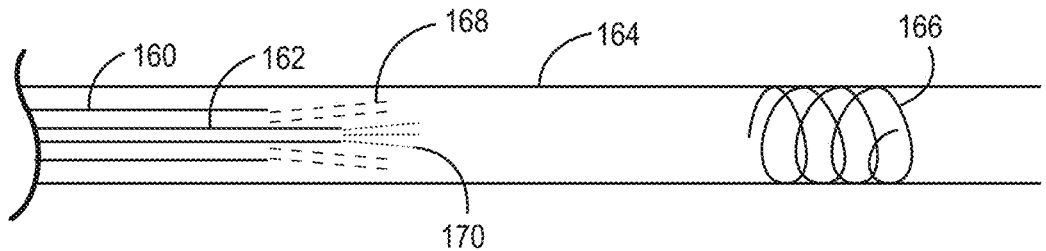
FIG. 6A depicts a use of an embodiment of an embolization system in combination with a hemostatic coil, with a first and a second embolic component being released from a first and a second lumen of a delivery device.
Figure 6B:
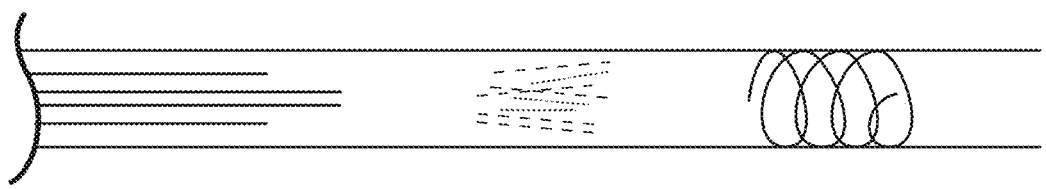
FIG. 6B depicts the use of FIG. 6A, with the first and second embolic components flowing towards the coil.
Figure 6C:
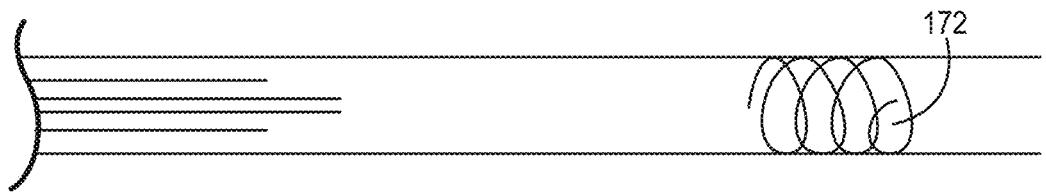
FIG. 6C depicts the use of FIG. 6B, with the first and second embolic components forming an embolization material at the coil.
Figure 6D:
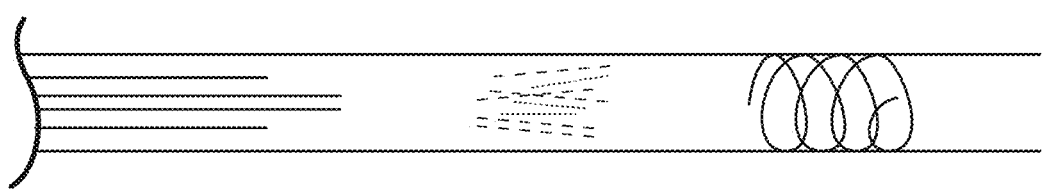
FIG. 6D depicts the use of FIG. 6C, with a second dose of the first and second embolic components flowing towards the coil.
Figure 6E:
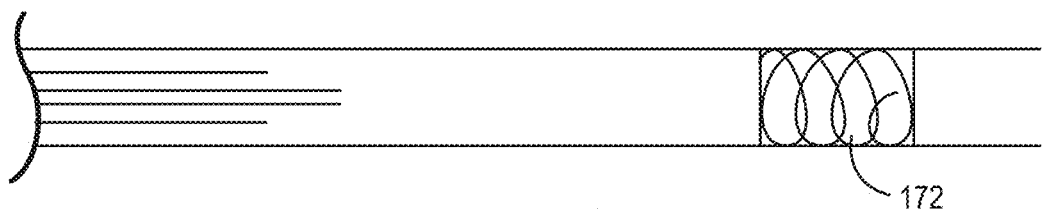
FIG. 6E depicts the use of FIG. 6D, with the vasculature being embolized with the embolization material at the coil.

An alternative method of embolization is depicted in FIG. 5 wherein first embolic component 146 is released from the annulus at tip 84 and second embolic component 148 is released at tip 26, with the first and second embolic component reacting to form an embolic material using, for example, an electrophilic-nucleophilic chemistry. Embolic domains 150 are formed and go downstream to embolize vascular bed 128.

Embolization materials may be used to treat vascular lacerations.

A method of using the embolic components with medical devices located in vivo is depicted in FIGS. 6A-6E. Catheters 160, 162 are introduced into vasculature 164 proximal to a target site wherein a medical device, e.g., coil 166 has been placed, for example through catheter 160. Embolic components 168, 170 are released and allowed to flow downstream to coil 166. Components 168, 170 react with each other to form embolization material 172. Multiple doses of components 168, 170 may be delivered until embolization material completes embolization of vessel 164. This process has been observed in experiments using a model flow chamber, including as described in Example 12, with various flow rates and tubing sizes that model the flow conditions in a blood vessel. The embolic components, their concentrations, and their rates of delivery were chosen so that they did not form an embolization material in the vessel unless there was an obstruction such as a coil placed in the tubing. The embolic material 172 was observed to form at and around the coil. Without being bound to a particular theory, it appears that the embolic components had begun to react to form a tenuous hydrogel before reaching the coil, and the coil anchored these tenuous structures so that they hydrogel could be built up. An alternative theory is that the coil promoted an irregular rheology as blood and the embolic components flowed across the coil, which promoted mixing and formation of the embolic material at the coil. It may be that both theories are correct and the particular circumstances dictate which of these effects is the greater. Many medical devices are available for placement in a vasculature and/or vascular anomaly, for instance, hemostatic coils, hemostatic plugs, and the like, e.g., beads, stents, filters, balloons, with all of the foregoing being available in metal, polymer based, biodegradable, and permanent forms.

Figure 7A:
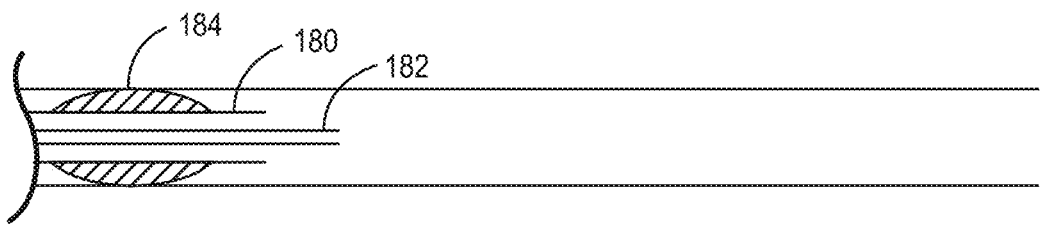
FIG. 7A depicts a use of an embodiment of an embolization system in a vasculature in combination with a balloon.
Figure 7B:
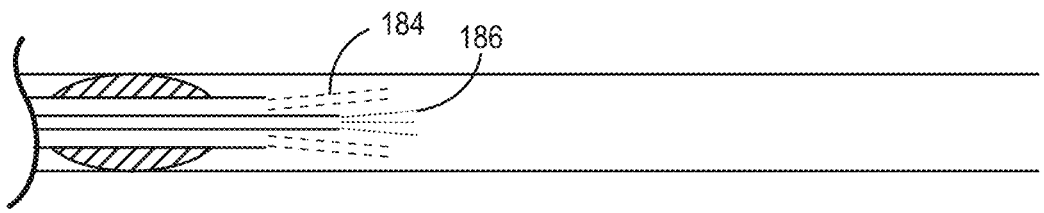
FIG. 7B depicts the use of FIG. 7A with embolic components being released from the delivery device.
Figure 7C:
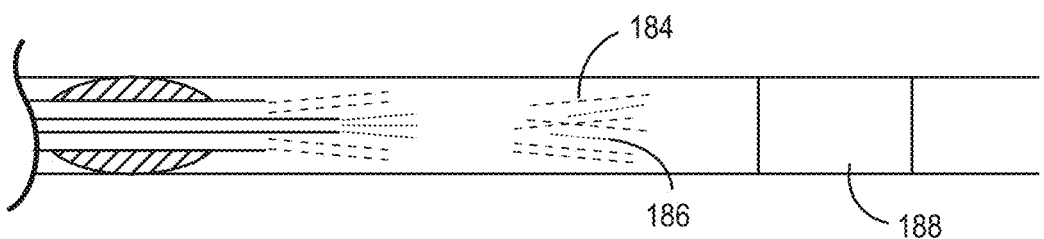
FIG. 7C depicts the use of FIG. 7B with the embolization material embolizing the vasculature.

An alternative method of using the embolic components is depicted in FIGS. 7A-7C. Catheters 180, 182 are placed near a target tissue and balloon 184 is fully deployed (as shown) or partially deployed. Embolic components 184, 186 are released from lumens of catheters 180, 182. Note that one of the catheter lumens in an outer catheter lumen and the delivery area is the annular space between the inner and outer catheters. Components 184, 186 react to form embolic material 188. This process was observed in experiments using a model flow chamber with flow rates and tubing sizes that model the flow conditions in a blood vessel. The embolic components and their concentrations were chosen so that they did not form an embolization material in the vessel in the absence of a flow restriction in the vessel. The embolic material 172 was observed to form only when balloon 184 was fully or partially deployed. As already described, the reduced blood flow rate apparently created conditions wherein the embolic components were concentrated relative to unrestricted flow conditions so that embolization material 184 could form. The fact that the embolic components could be chosen to avoid forming an embolization material under a first set of dilution conditions (when there was no flow restriction) was successfully exploited to create new methods of using the materials so that the embolizing materials were formed only under restricted flow conditions. Further, forming an embolic gel in concert with a coil under stasis may produce a more concentrated gel relative to forming gel in a coil with unrestricted blood flow.

As is customary in these arts, the term catheter is used in some contexts to refer to the entire catheter as assembled or to the catheter shaft, as is evident from the context of the term. The distal outlets of the catheter lumens deliver fluids or provide access to the patient for tools and the proximal portion of the catheter is exterior to the patient during use. One-way valves may be provided in series with the lumens, e.g., to block backflow. Delivery may be applied manually or by machine force. An example of a manual fluid supply is a syringe operable by manual force. Syringes may be independently operable or connected to operate together when a single force is applied. For instance a dual or multi-barreled syringe may be operate manually or with a syringe pump. Another example of a reservoir is a pressurized container or a container connected to a pump, e.g., a peristaltic pump. The rate of flow from the fluid supply may be constant, adjustable for different flow rates, or adjustable to change flow rates while the catheter is in use. Controls for pulsatile flow may be provided to regulate one or more of a flow rate, a volume, a time of flow, and a time between pulses. The controls may be mechanical, e.g., a cam or ratchet, or electronic, e.g., by electronic control of a mechanically operable pump. The pulses may be set to correspond to partial doses described herein or to a fixed dose. The fluid supplies may be used to supply liquids that contain embolic components and other components useful for embolic processes. Preferred sizes for catheters and useful embolic components are described below.

Experimentation indicated that slidable catheter systems such as coaxial catheter systems can be used advantageously, with one catheter being placed to release an embolic component distally relative to another catheter that releases a different embolic component. Coaxial catheters as exemplified in FIGS. 1-3 are slidable catheters and have two catheter shafts that are movable relative to each other. In use, the distance, represented as d in FIG. 3, may range from more than 0 to 100 mm; artisans will immediately appreciate that all ranges and values between the explicitly stated bounds are contemplated: 0.1, 0.5, 1, 2, 3, 4, 5, 6, 7, 8, 9, 10, 15, 20, 25, 30, 40, 50, 75, or 100 mm, e.g., 2-10 mm or 3-7 mm. A useful range for this offset distance for embolizing a hypervascular tumor is typically 3-10 mm or 3-7 mm. In the case of treatment of a vascular laceration, an offset distance is, for example 0-15 mm and artisans will appreciate that all the ranges and values therebetween are contemplated, as already enumerated.

WORKING EXAMPLES

Example 1 describes an in vivo test using a rabbit animal model with kidneys being embolized as a model vascular bed. One embolic precursor was a first liquid containing a polymerizable water soluble polymer linear polyethylene glycol (PEG) diacrylate 3.4 kDa (Mn) at 30% w/w concentration dissolved in 1% w/w ferrous gluconate(aq) (FeG) that was delivered through the inner catheter. The other embolic precursor was a second liquid containing a free radical polymerization initiator (tert-butyl peroxide, TBHP, 1000 ppm) and iopromide as a contrast agent that was delivered through the annulus between the inner catheter and outer catheter. These treatments reflect a test of a redox initiated polymerizable system for embolization. The size of a rabbit kidney approximates that of a tumor in the liver of human with typical size 1-5 centimeters in diameter, which is a typical size for a hypervascular tumor. The inner catheter tip was used a distance of 5 mm distal to the other catheter tip. The two compositions were delivered at a 1:1 v/v ratio. Embolization of the targeted vasculature was successful, including embolization of small (less than 15 μm diameter) vessels. The term nominal concentration used herein a refers to a concentration of an embolic component or other material that results when it is diluted in the proportion at which it is delivered. In the case of an in vitro test, components mixed at a 1:1 v/v proportion have a nominal concentration that is half of the concentration as-prepared. In an in vivo reaction, embolic components prepared at a first concentration and then delivered at a 1:1 v/v ratio result in a nominal concentration that is half of the as-prepared concentration.

Example 2 used the same materials as Example 1 but the embolic compositions were delivered at a location where the compositions were intentionally allowed to flow both into the target tissue (kidney) and off-target tissue (into the cranial mesenteric artery). The target tissue was embolized but the off-target tissue was not embolized. Without being bound to a particular theory, it is believed that the rate of dilution of the embolic components was higher in the mesenteric artery such that the embolic components were diluted before they could react with each other. In contrast, dilution in the kidney was apparently taking place at a lesser rate so that embolization was effective.

A different formulation of embolic material was used in Example 3. Further, the delivery technique was modified to change from a bolus to an intermittent delivery technique referred to as Puff in the Examples. The Puff technique has an advantage of allowing the user to administer a portion of a desired dose of embolic components and assess the results in real-time imaging, usually within several seconds. The user can continue intermittent administration until a desired end result is achieved. In general, many conventional embolization techniques use materials and processes that do not allow for a rapid assessment of the results such that the user has to wait many minutes, or even longer, to assess if the procedure is effective and how to respond if the results are not satisfactory.

The formulation of Example 3 used a first liquid with a 10 kDa (Mn) PEG diacrylate at a 12% w/w concentration as-prepared (6% w/w nominal concentration) and 0.88% w/w ferrous gluconate. The second liquid contained 2830 ppm TBHP in ULTRAVIST 300 solution. ULTRAVIST 300 is a well-known nonionic, water soluble x-ray contrast agent; each mL provides 623.4 mg iopromide, with 2.42 mg tromethamine as a buffer and 0.1 mg edetate calcium disodium as a stabilizer. It is significant that these embolic chemistries are effective in a variety of conventionally available x-ray contrast agent media, since this allows users to choose a medium that is compatible with their existing processes for imaging and the like.

A set of formulations described in Example 4 used a water soluble hydrogel precursor at a variety of concentrations and molecular weights, ranging from 3.4 kDa to 10 kDa (Mn) and 7.5 to 15% w/w nominal concentrations. Other variables were held constant. Example 4 also describes the in vitro gel time test. Gel time, in general, became faster in response to increased concentrations of vinyl moieties, polymerization initiator and reductant. But gel times may also became faster as the molar concentration of the acrylate functional water soluble polymer (PEG diacrylate) was decreased by increasing the PEG molecular weight, Table 1. This result is counter-intuitive since gel times would be generally expected to be accelerated when there is an increase in functional group (acrylate) concentration. This counter-intuitive result is useful for making dilution-sensitive embolic compositions that nonetheless gel quickly. Without being bound to a particular theory, this result is attributed to an increasing ability to form micelles with increasing molecular weight (MW). The micellar formation creates areas enriched with acrylate moieties.

A second set of formulations, Table 2, used a concentration of a peroxide (specifically, TBHP) ranging from 1000-3000 ppm and a concentration of reductant (FeG) ranging from 1-2% w/w, with other variables being held constant. Gel times were, in general, decreased as the concentrations of initiator and reductant were increased. It can be seen that increasing FeG concentration from 1.5 to 2 had little effect on gel time. The number of functional groups in a multiple armed precursor had little effect on gel times, with systems having precursors with 2 arms versus 4 arms both gelling in less than 1 second, Example 7.

Example 5 demonstrates dilution sensitivity of embolic components. The embolic components, at the indicated conditions, were observed to be dilutable by 300% v/v to prevent gelation. The exact amount to prevent gelation can be estimated from Table 3, which reports a nominal 6% PEG solution failing to gel at 3% or 2% nominal concentrations dependent on the initiator that is used, which corresponds to a 100% or a 200% v/v dilution, respectively. Example 6 further demonstrates dilution sensitivity of embolic components observed to be dilutable by 300% v/v to prevent gelation. As reported in Table 4, the 6% nominal PEG solution failed to gel at a nominal concentration of 2.4%, which is a 150% v/v dilution.

Examples 8 and 9 are further working examples of successful embolization. These Examples used a two-part electrophilic-nucleophilic functionalized precursor system for embolization. Examples 10-11 tested the cohesivity and adhesivity of the embolic materials. The materials were not adherent to tissues, and had low or no adherence to plastic tubing, and catheters. Example 12, discussed above, demonstrated that the embolic components could be used, when desirable, to form an embolic material only at the site of a medical device or a targeted obstruction in a lumen.

It was observed that the embolization components were deliverable to embolize large and small vessels, with branches of vessels being embolized in a vascular area that had multiple branches. A quantity and rate of delivery may be used to embolize blood vessels of a desired diameter, e.g., blood vessel diameters from 4 µm to 15 mm; Artisans will immediately appreciate that all ranges and values between the explicitly stated bounds are contemplated, e.g., less than 10 or less than 20 µm, 4, 8, 10, 15, 20, 30, 50, 100, 200, 500, 1000, 1500, 2000 µm, from 4-50 µm, at least 10 µm, at least 15, or at least 20 µm; or 1, 2, 3, 4, 5, 10, or 15 mm. The hydrogels, once formed at the target location, evidently swelled to block any remaining channels, voids, or areas between the embolic material and edges of the blood vessels.

Dilution of embolic components presents certain challenges to making an embolic material, including the challenge that embolic components will not react to make a material that is well-formed enough to block blood flow. Surprisingly, however, the experiments showed that the components could be released in a blood vessel and occlude multiple branches of the vessel. The hydrogels were formed with adequate mechanical strength and in continuous form that retarded flow of blood or fluids.

Once this theory was appreciated, various factors of the system were available to further exploit this discovery. One factor was an adjustment of a distance between the points of release of the embolic components by controlling a distance between a distal outlet of an inner catheter and a coaxial outer catheter distal outlet. The distance between these outlets, which were at the tips of the catheters used in the Examples, could be controlled to provide a dilution effect that was favorable. In this aspect, it was unexpected and surprising to discover that certain dilution effects provided unforeseen advantages. Without being bound to a particular theory, it is believed that fluids containing the embolic components initially released into flowing blood were partially diluted and combined to form multiple small domains and/or hydrogels that flowed into branches of the vasculature wherein they provided embolization. Accordingly, certain embodiments of the invention include one or more of releasing embolic forming components from a multi lumen catheter with a distance between the distal tips, using dilution sensitive embolic compositions, embolic compositions that polymerize quickly (approximately ≤5 sec), release of embolic components in partial doses, and chemistries useful to perform in these contexts for effective embolization, including embolization of hypervascular tumors (benign, cancerous) and vascular lacerations. These and other features are described in detail below.

Challenges to forming an effective embolic system as described herein included dilution of embolic components in flowing blood, adequate mixing of the components for effective reaction, and substantially filling the vascular vessels with the hydrogel to provide a complete blockage of blood flow through the vessels. Besides these challenges, embolic systems were further created with mechanism wherein ongoing dilutive effects prevented formation of an embolic material at sites other than the intended target tissues. Furthermore, embolic hydrogels could be formed as cohesive materials in tissue, vascular tissue, organ tissue, plastic tubing, and catheters. The hydrogels were cohesive to themselves and not adherent to tissues. The cohesive property provides an important safety feature because a device such as a catheter used to deliver the hydrogel will not become stuck in the hydrogel, if encased in embolic hydrogel material. There is a further advantage that became evident upon experimentation with these systems: catheters could be used in the patient for a series of embolic treatments so that a plurality of locations could be embolized without removal and replacement of the catheter. And progress of the embolization could be monitored and repeated doses administered as desired.

Further Disclosure of Embolic Materials, Precursors, Functional Groups, and Hydrogels Embolic materials should ideally be easily delivered in a controlled fashion and avoid non-target embolization. These materials should form durable occlusions and be composed of biocompatible materials suitable for implantation.

The embolic materials comprise a matrix that is formed of crosslinked precursors. The term precursor refers to components that crosslink to form the matrix. Materials that are present in the matrix but are not reacted to form the matrix are not precursors, e.g., salts or imaging agents. The embolic material is preferably a hydrogel that has a crosslinked matrix formed of precursors covalently reacted with each other to form the matrix. Precursors are chosen in consideration of the properties that are desired for the resultant embolic material, e.g., a hydrogel. Hydrogels have matrices hydratable to have a water content of more than about 20% w/w; Artisans will immediately appreciate that all ranges and values between the explicitly stated bounds are contemplated, with any of the following being available as an upper or lower limit: 20%, 99%, 80%, 95%, at least 50%, and so forth, with the percentages being w/w and the solvent being water for hydrogels. The matrices may be formed by crosslinking water soluble molecules to form networks of essentially infinite molecular weight. Hydrogels with high water contents are typically soft, pliable materials. Hydrogels are described in U.S. Publication Nos. 2009/0017097, 2011/0142936 and 2012/0071865.

Precursors comprise a functional group or groups for reaction to produce a covalently crosslinked matrix. A group is a chemical moiety that provides the characteristic chemical reaction of the molecule. The term group is used to indicate that the molecule bearing the group is freely derivitizable or substitutable with other chemical moieties. The term functional group is used herein to refer to a group of one or more atoms of distinctive chemical properties no matter what they are attached to. The atoms of functional groups are linked to each other and to the rest of the molecule by covalent bonds. The term functional group in the context of forming an embolic material refers to the groups that undertake the covalent bonding to form the matrix of the embolic material, with a functional group undergoing a covalent bonding reaction with another functional group to make a covalently crosslinked matrix. To form crosslinked matrices, a precursor must react with another precursor at a plurality of tie points. In general, a precursor molecule in a matrix is joined to other precursor molecules at two or more points. Precursors with at least two functional groups that are reactive centers (for example, in free radical polymerization) can crosslink since each reactive group can participate in the formation of a different growing polymer chain. In the case of functional groups without a reactive center, among others, crosslinking requires three or more such functional groups on at least one of the precursor types. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups.

Polymerizations with Oxidation-Reduction (Redox) Reactions

Polymerization chemistries with redox reactions are useful for reaction of embolic compositions. Experimentation indicated that fast-polymerizing conditions advantageously form domains in flowing blood without trapping the delivery catheter. Fenton's type reagent is a mixture of peroxide and iron. Polymerization with redox reactions such as Fenton's reagents or by Fenton's type chemistry is a term used herein to describe the use of a peroxide in a presence of a reductant to polymerize a free-radical polymerizable functional group to cause polymerization of a precursor to form an embolic material. The formation of a hydrogel is preferable as the embolic material. Precursors and functional groups are discussed elsewhere herein. Preferred free radical polymerizable functional groups are acrylates and derivatives of acrylates. A free radical polymerization process involving redox reactions involves a reductant to catalyze a peroxide to form free radicals. Peroxides for use as initiators include organic peroxides and inorganic peroxides. Organic peroxides are organic compounds containing a peroxide functional group (ROOR'). If the R' is hydrogen, the compounds are called organic hydroperoxides. Peresters have general structure RC(O)OOR. Organic peroxides can be divided into classes such as peroxyesters, peroxy(di)carbonates, diacyl peroxides, dialkyl peroxides, peroxyketals and hydroperoxides. The O—O bond easily breaks, producing free radicals of the form RO.. TBHP was used in the Examples as an exemplary peroxide. Examples of peroxides peroxide forming materials are hydrogen peroxide, sodium persulfate, tert-amyl hydroperoxide, ammonium persulfate, potassium persulfate, and solid peroxides that form a peroxide, e.g., hydrogen peroxide, upon mixture with aqueous media. Solid peroxides include, for example, urea hydrogen peroxide, sodium percarbonate and sodium perborate. A concentration of an initiator is typically from 10 to 10,000 parts per million (ppm); artisans will immediately appreciate that all ranges and values between the explicitly stated bounds are contemplated, e.g., 10, 20, 30, 40, 50, 100, 150, 200, 250, 300, 400, 500, 600, 700, 800, 900, or 1000 ppm, or from 100-2000 ppm or 100-1000 ppm.

In certain embodiments, one embolic component comprises a polymer with co-initiator and a second embolic component comprises an initiator. A reductant may be present in an embolic component that does not contain a peroxide. A fluid that contains one of the embolic components is combined with a fluid containing the other embolic component to make the embolic material, with one or both fluids containing a reductant, which may be present as a single species (one of the di- or trivalent ions) or as multiple species (at least two different reductants). Reductants include a metal ion, e.g., $Fe^{2+}$, $Cr^{2+}$, $V^{2+}$, $Ti^{3+}$, $Co^{2+}$, and $Cu^+$. These may be provided in compounds or as salts, e.g., an iron salt, iron compounds, ferrous sulfate, ferrous lactate, ferrous gluconate, and a copper salt. Salts may include sulfates, chlorides, potassium, succinates, and the like. A concentration of a reductant ion in an embolic fluid is typically from 0.2 to 200 mM; artisans will immediately appreciate that all ranges and values between the explicitly stated bounds are contemplated, e.g., 0.2. 1, 5, 10, 15, 19, 20, 21, 25, 30, 35, 40, 50, 75, 100, 150, 200 mM, or from 10 to 50 mM.

It is useful to use a commercially available radiopaque reagent as a diluent for an embolic component. For instance a peroxide may be placed in combination with a commercially available radiopaque agent. These agents include but are not limited to OMNIPAQUE (iohexol), ISOVUE (iopamidol), OPTIRAY (ioversol), and ULTRAVIST (iopromide). An embolic component may comprise a one of these regents and a peroxide or a reductant.

A free-radical polymerizable group comprises an unsaturation such as an unsaturated hydrocarbon group, e.g., a vinyl group. Free-radical polymerization is a successive addition of monomers to a growing chain. Free radicals can be formed in response to initiators. An initiated free radical has an active center and adds itself to other monomer units to grow the polymer chain. Monomers are preferably an unsaturated hydrocarbon or a vinyl group ($-CH=CH_2$). Vinyl groups may be used as functional groups on a precursor, e.g., a polymer may be derivatized to carry a vinylic functional group. Vinylic functional groups include acrylate groups and methyl acrylate. The term group refers to a chemical moiety that may be substituted, and the substituents may, in turn, be substituted. Derivatives of an acrylate group include a methacrylate group.

Electrophile-Nucleophile Chemistries and Functional Groups

Embolic materials may be made with embodiments that involve a covalent reaction between an embolic component that comprises an electrophilic functional group and an embolic component that comprises a nucleophilic functional group. A nucleophilic group is a chemical species that donates an electron pair to an electrophile to form a chemical bond in relation to the reaction. An electrophilic group is a chemical group with a tendency to react with a nucleophilic functional group containing a donatable pair of electrons. The embolic components comprising the electrophilic or nucleophilic groups may be precursors as described below, e.g., polymers, small molecules, or other molecules. The embolic components react with each other to form the embolic material.

As described in Example 8, precursors with electrophilic and nucleophilic functional groups may be provided in one of the embolic components under conditions where they are not reactive with each other, e.g., at a first, low pH. Another of the embolic components may have a factor that adjusts a pH of the combined components to achieve a second pH that is favorable for a covalent reaction of the functional groups, e.g., an alkaline buffer. An embodiment of an embolization system for controlling solidification in vivo of embolic compositions is one comprising: a first fluid supply containing a first liquid at a first pH that comprises a precursor comprising a plurality of electrophilic functional groups a precursor that comprises a plurality of nucleophilic functional groups, a second fluid supply containing a second liquid that, when mixed at a 1:1 v/v ratio with the first liquid, causes the mixture of the first fluid and the second fluid to have a second pH favorable for reaction of the electrophilic functional groups with the nucleophilic functional groups, a catheter adaptor connectable to the first fluid supply for delivery of the first liquid to a first catheter lumen and connectable to the second fluid supply for delivery of the second liquid to a second catheter lumen, wherein a 1:1 v/v mixture of the first liquid and the second liquid provides for the electrophilic groups and the nucleophilic functional groups to react with each other to covalently crosslink the precursors to form an embolization material. In this embodiment, a predetermined dilution of the mixture of the first liquid and the second liquid may be chosen that prevents formation of the embolic material or prevents formation of the embolic material for a predetermined time. For instance the dilution may be chosen from a range of 100%-400% v/v dilution of a 1:1 v/v mixture of the first liquid and the second liquid prevents formation of the embolization material as measured by a failure to form the embolization material within a predetermined time chosen from a range of 20 to 600 seconds in an in vitro gel time test. Embodiments of the embolization system may include certain embodiments wherein the first and the second fluids provide a stoichiometric ratio ranging from 0.9:1 to 1.1:1 for the electrophilic groups to the nucleophilic groups when the first and the second liquids are mixed 1:1 v/v. The first pH may be chosen from a range of less than 7 or from 0.1 to 7.0; artisans will immediately appreciate that all ranges and values between the explicitly stated bounds are contemplated, e.g., a pH of 2-5, 3, 4, 5, 6, or 7. The second pH may be chosen from a range of at least 7 or 7-14; artisans will immediately appreciate that all ranges and values between the explicitly stated bounds are contemplated, e.g., 7.0, 7.2, 7.4, 8, 9, 9.5, 10, 11, 12, 13, and 14.

Amines and thiols are preferred nucleophilic functional groups. A range of electrophilic functional groups are available to make fast and efficient reactions. Carboxylic acids, do not normally react with other groups, such as amines or thiols, under physiological conditions. However, such groups can be made reactive by derivatizing them with an activating group such as N-hydroxysuccinimide to create an activated ester. Several methods for activating such functional groups are known in the art. Preferred activating groups include carbonyldiimidazole, sulfonyl chloride, aryl halides, sulfosuccinimidyl esters, N-hydroxysuccinimidyl ester, succinimidyl ester, epoxide, aldehyde, maleimides, and imidoesters. Polymers with hydroxyl and/or carboxyl groups are, in general, readily derivitizable into a functional group.

Succinimide groups are useful electrophilic functional groups and reactions with functional groups such as amines and/or thiols are preferred. Succinimide groups include succinimidyl esters, N-hydroxysuccinimide groups, N-hydroxysuccinimide ester groups, sulfosuccinimide groups, sulfosuccinimide ester groups N-hydroxysulfosuccinimide ester groups, N-hydroxyethoxylated succinimide ester groups, N-hydroxysuccinimidyl glutarate (SG), N-hydroxysuccinimidyl succinate (SS), N-hydroxysuccinimidyl carbonate (SC), N-hydroxysuccinimidyl adipate (SAP), or N-hydroxysuccinimidyl azelate (SAZ). Some of these groups have esteric linkages that are hydrolytically labile and relatively more linear hydrophobic linkages such as pimelate, suberate, azelate or sebacate linkages may also be used, with these linkages being less degradable than succinate, glutarate or adipate linkages. Branched, cyclic or other hydrophobic linkages may also be used. Further electrophilic functional groups are for instance: carbodiimidazole, sulfonyl chloride, chlorocarbonates, maleimide.

Precursors

An example of a precursor is a multifunctional precursor. The term multifunctional refers to having at least two functional groups, for instance more than 2 or from 2-200 functional groups. Artisans will immediately appreciate that all ranges and values between the explicitly stated bounds are contemplated, 2, 3, 4, 5, 6, 7, 8, 9, 10, 11, 12, 13, 14, 15, 16, 20, 26, 32, 50, 60, 64, 70, 80, 90, 96, 100, 110, 112, 120, 128, 140, 150, 160, 180, 190, or 200, or 2-16 or 2-8.

The multifunctional precursor may be a polymer or a non-polymer. A polymer is a molecule made of a series of repeating units referred to as monomer units or residues. Polymers include random, block, alternating block, random block, and copolymers. The term polymer is used to include oligopolymers, which is used herein to refer to polymers having no more than 20 repeat units. A polymer has at least three repeat units. A non-polymer may be used. Some non-polymers are useful as crosslinkers, e.g., a non-polymer precursor having a molecular weight (Mn) of 2000 or less. The multi-functional precursor (polymer or other precursor) may be water soluble, meaning that it is soluble in aqueous solution at room temperature at a concentration of at least 1 g/100 ml. A water soluble precursor has an advantage that a droplet of the precursor is subject to continued dilution, dispersion and clearance from the body if it is not reacted, relative to a hydrophobic precursor that may form a hydrophobic liquid particle that might embolize at an unwanted location. The precursor may be a water soluble polymer or a water soluble non-polymer.

A multifunctional precursor may comprise a core and a plurality of arms. The core is a term that refers to a contiguous portion of a molecule joined to the plurality arms that extend from the core, with some or all of the arms having a functional group, which is often at a terminus of the arm. The core and/or one or more of the arms may be hydrophilic and chosen from the various precursors set forth herein. A number of arms may be, for instance, more than 2 or from 2-200 functional groups. Artisans will immediately appreciate that all ranges and values between the explicitly stated bounds are contemplated, 2, 3, 4, 5, 6, 7, 8, 9, 10, 11, 12, 13, 14, 15, 16, 20, 26, 32, 50, 60, 64, 70, 80, 90, 96, 100, 110, 112, 120, 128, 140, 150, 160, 180, 190, or 200. About 2-16 arms are generally preferred due to steric consideration at molecular weights considered for this application. 2 arms refers to a linear non-branched polymer. A hydrophilic arm may be, for instance, a polyether, for example, a polyalkylene oxide such as polyethylene glycol (PEG), polyethylene oxide (PEO), polyethylene oxide-co-polypropylene oxide (PPO), co-polyethylene oxide block or random copolymers. As is customary in these arts, the term PEG is used to refer to a polymer with repeating PEO groups regardless of the end group of the PEG. A hydrophilic arm or core may comprise, for instance, a polyvinyl alcohol (PVA), poly (vinyl pyrrolidinone) (PVP), poly (amino acids), dextran, or a protein. The term multifunctional precursor comprising a core and a plurality of arms is limited to a precursor of molecular weight of less than 250,000 Daltons (Mn). A multifunctional precursor comprising a core and a plurality of arms may have, e.g., a core that is no more than 10% or 20% w/w of the total weight of the precursor; artisans will immediately appreciate that all ranges and values between the explicitly stated bounds are contemplated: 1, 2, 5, 10, 15, or 20%, with Mn being used. The term hydrophilic means that the portion that is hydrophilic is water soluble, or would be water soluble if not otherwise attached to other materials, according to the definition of that term set forth herein.

A multifunctional precursor may comprise a backbone and a plurality of pendant groups with the precursor having two or more functional groups. Many polymers have a structure resulting from the creation of a polymer referred to as a backbone that is modified by adding pendant groups that are attached to the polymer backbone. The backbone is the polymer that is modified by the addition of a plurality of pendant groups. The polymer backbone serves as a group that can be substituted or derivatized and the pendant groups may be further decorated with pendant groups or substituted and derivatized.

A multifunctional precursor may be, or may comprise, a hydrophilic polymer, or may consist essentially of a hydrophilic polymer. The term consisting essentially, in the context of a precursor, means that the precursor is at least 80% by weight of the indicated polymer residue. For instance, a PEG polymer that is made up by at least 80% w/w polyethylene oxide groups ($CH_2CH_2O$) consists essentially of PEG. A PEG content of a polymer or arm is calculated by adding up all of the polyethylene oxide groups on the polymer or arm, even if they are interrupted by other groups. Thus, an arm having at least 1000 MW polyethylene glycol has enough $CH_2CH_2O$ groups to total at least 1000 MW. Examples of hydrophilic polymers are PEG, poly(vinyl alcohol), hyaluronic acid, poly(vinylpyrrolidone) (PVP), polyethers, poly (oxyalkylenes), and polyalkyleneimines, as well as copolymers and derivatives thereof, including substitutions thereof. As is customary in these arts, the term PEG is used to refer to polyethylene oxide with or without hydroxyl end groups and regardless of particular end groups.

A multifunctional precursor may be made with a hydrophobic portion and may be used to make a hydrogel provided that the resultant hydrogel retains the requisite amount of water of at least about 20%. In some cases, the precursor is nonetheless soluble in water because it also has a hydrophilic portion. Similarly, some amount of a hydrophobic precursor may be used in combination with a hydrophilic precursor to make a hydrogel provided that a hydrogel is the result. A hydrophobic precursor may make a dispersion in the water (a suspension) but be nonetheless reactable to from a crosslinked material. Some hydrophobic portions may include a plurality of alkyls, polypropylenes, alkyl chains, or other groups. Some precursors with hydrophobic portions are sold under the trade names PLURONIC F68, JEFFAMINE, or TETRONIC. A hydrophobic molecule or a hydrophobic portion of a copolymer or the like is one that is sufficiently hydrophobic to cause the molecule (e.g., polymer or copolymer) to aggregate to form micelles or microphases involving the hydrophobic domains in an aqueous continuous phase or one that, when tested by itself, is sufficiently hydrophobic to precipitate from, or otherwise change phase while within, an aqueous solution of water at pH from about 7 to about 7.5 at temperatures from about 30 to about 50° C.

A multifunctional precursor polymer may be a natural or synthetic material. The term natural means found in nature in a plant, animal, or eukaryotic cell. The term includes derivatized natural products, and also include natural materials purified from natural products made synthetically or by recombinant means. Natural polymers thus include glycosaminoglycans, polysaccharides, and proteins. Some examples of glycosaminoglycans include dermatan sulfate, hyaluronic acid, the chondroitin sulfates, chitin, heparin, keratan sulfate, keratosulfate, and derivatives thereof. These materials may be modified synthetically from a naturally soluble state to a partially soluble or water swellable or hydrogel state. Natural proteins or polysaccharides may be adapted for use with these methods, e.g., proteins, peptides, polysaccharides, collagens, fibrin(ogen)s, albumins, alginates, hyaluronic acid, and heparin.

Synthetic precursors may be used. Synthetic refers to a molecule not found in nature in a plant, animal, or eukaryotic cell. Some synthetic precursors are free of amino acids or free of amino acid sequences that occur in nature. Some synthetic precursors are peptides, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derivatized thereof. The backbone of such an oligopeptide may be natural or synthetic. In some embodiments, peptides of two or more amino acids are formed as part of a synthetic backbone to make a precursor.

Precursors with a molecular weight of no more than 2000 Daltons are useful and can advantageously be used in combination with precursors that have a molecular weight of at least 4000 Daltons. Artisans will immediately appreciate that all ranges and values between the explicitly stated bounds are contemplated, with no more than 2000 including 100-2000, 200, 300, 400, 500, 600, 700, 800, 900, 1000, 1500 and 1990 Daltons (Mn); and also with at least 2000 including 2000-1,000,000 Daltons (Mn).

Multi-functional precursors may be prepared to be free of amino acid sequences cleavable by enzymes present at the site of introduction, including free of sequences susceptible to attack by peptidases and/or metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and cannot be made by cleaving a naturally occurring protein and cannot be made by adding synthetic materials to a protein. Precursors may be non-collagen, non-fibrin, non-fibrinogen, and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight. Thus a precursor may, for example, exclude hyaluronic acid, heparin, or gellan. Precursors can also be both non-proteins and non-saccharides.

Precursors and the resultant embolic materials may be degradable hydrolytically, enzymatically, or non-biodegradable. The term biodegradable refers to conditions typical to an implant in a human body and encompasses both hydrolytically degradable groups and proteolytically degradable groups. Hydrolytically degradable groups are groups that spontaneously degrade in water: esters are hydrolytically degradable. Proteolytically degradable groups are groups degraded by proteases. Proteolytically degradable amino acid sequences are known that are degradable by proteases, e.g., collagenases or metalloproteinases, and may be incorporated into a precursor to provide proteolytic degradability. Hydrocarbon chains, polycarbonates, and PEGs are not biodegradable. Polyamides that lack proteolytically degradable sequences are not biodegradable and, unanalyzed, hydrolysis of amide or peptide bonds is extremely slow. Implants that are not degraded to a point of losing at least two-thirds of their mechanical strength after implantation for twenty years in a human are non-degradable. Certain embodiments of biodegradable materials are non-biodegradable polymers that have one or more functional groups linked to the polymer by a biodegradable group, e.g., an ester or other hydrolytically degradable groups or an enzymatically degradable group.

A multifunctional precursor comprises a plurality of functional groups. An embodiment of a multi-functional precursor is a hydrophilic polymer or a non-polymer. One or more multifunctional precursors may be used to form an embolic material. The multifunctional precursor is preferably chosen to form a hydrogel and is hydrophilic or is used in combination with other multifunctional precursors that are hydrophilic to form a hydrogel. The multifunctional precursor may comprise one or more biodegradable groups or be free of biodegradable groups. The multifunctional precursor may be chosen to have a number of functional groups and/or arm or pendant groups as described herein. The functional groups may be a free-radical polymerizable functional group, an electrophilic functional group, or a nucleophilic functional group. A molecular weight of the multifunctional precursor may range from 100-1,000,000 Daltons (Mn). Artisans will immediately appreciate that all ranges and values between the explicitly stated bounds are contemplated, such as 100, 200, 300, 400, 500, 600, 700, 800, 900, 1000, 2000, 3000, 4000, 5000, 6000, 7000, 8000, 9000, 10,000, 15,000, 20,000, 25,000, 30,000, 40,000, 50,000, 60,000, 80,000, 100,000, 200,000, 250,000, 500,000, 700,000, 800,000, 900,000 Daltons (Mn). In general, molecular weights of less than 100,000 or less than 60,000 are preferred. A desired distance between crosslinks of the hydrogel or other embolic material is a consideration in a choice of molecular weights of the one or more precursors, and other properties are a consideration including solubility of the precursors, viscosity of a liquid used to deliver the precursor, and polymerization or other reaction kinetics that are affected by molecular weight. A number of functional groups for a multifunctional precursor is at least 2 or from 2-200. A number of arms on a multifunctional precursor may be from 0-200, e.g., more than 2 or from 2-200, with each arm having a functional group or a plurality of arms having a functional group, e.g., more than 2 or from 2-200. The arms of a multifunctional precursor may comprise one or more biodegradable groups or be free of biodegradable groups.

Multifunctional precursors that comprise a plurality of amines and/or thiols are generally useful for reaction with a multifunctional precursor that comprises electrophilic functional groups. Such precursors may have a molecular weight of less than 1000 or less than 2000 Daltons (Mn) may be chosen from, e.g., ornithine, spermine, spermidine, urea, guanidine, diaminopimelic acid, diaminobutyric acid, methylornithine, diaminopropionic acid, cystine, lanthionine, cystamine, trioxatridecanediamine, cyclohexanebis(methylamine), tetraethylenepentamine, pentaethylenehexamine, methylenebis(methylcyclohexamine), diaminocyclohexane, n-(2-aminoethyl)-1,3-propanediamine, diaminomethyldipropylamine, iminobispropylamine, bis(hexamethylene)triamine, triethylenetetramine, bis (aminopropyl)ethylenediamine, bis(2-aminoethyl)-1,3- propanediamine, bis(aminopropyl)propanediamine, diamniomethylpropane, 1,2-diamino-2-methylpropane, 1,3-diaminopentane, dimethylpropanediamine, 2,2-dimethyl 1,3-propanediamine, methylpentanediaminea, 2-methyl-1,5 pentanediamine, diaminoheptane, diaminooctane, diaminononane, diaminodecane, and diaminododecane.

Hydrogels for Embolic Materials

The embolic material may be a hydrogel. A hydrogel's structure may be described in terms of its matrix contents and/or properties, such as and the concentration of, and material composition of, the hydrogel's precursors. Embolic components used to make the embolic material may include precursors and/or initiators. Precursors properties include chemical composition, water solubility, hydrophilicity, molecular weight, arm length, number of arms, functional groups, distance between crosslinks, degradability, and the like. The choice of reaction conditions also effects the hydrogel's structure and properties, including choices of reaction chemistries, reactant concentrations, and solids content.

The spacing between molecular strands of the hydrogel (the matrix) affects several hydrogel properties. The crosslinking density can be controlled by the choice of the overall molecular weight of the precursor(s) used as crosslinker(s) and other precursor(s) and the number of functional groups available per precursor molecule. Yet another method to control crosslink density is by adjusting the stoichiometry of nucleophilic functional groups to electrophilic functional groups or concentration of redox initiators/co-initiators. Precursors with longer distances between crosslinkable sites form gels that are generally softer, more compliant, and more elastic as the crosslink density is lower i.e., higher average molecular weight between crosslinks.

Figure 8:
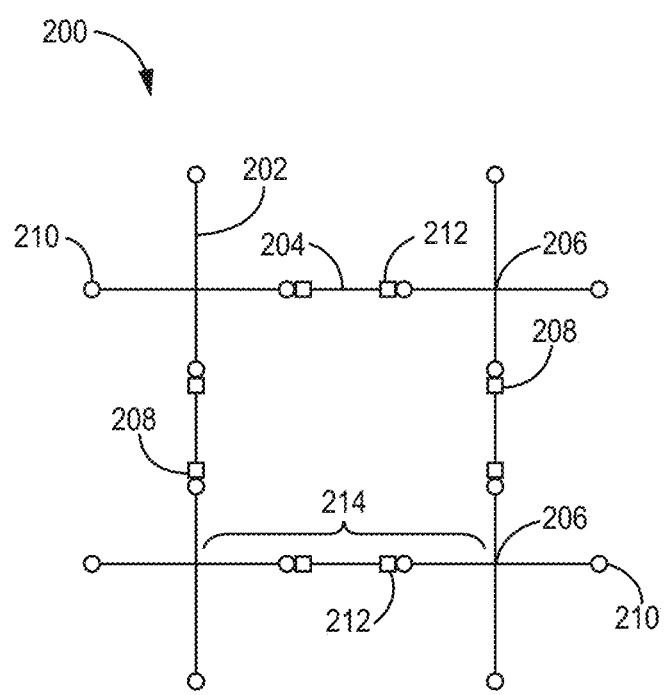
FIG. 8 depicts a portion of a matrix of crosslinked polymers, illustrating a calculated distance between crosslinks.

Precursors may be chosen with a geometry and structure to provide a calculated distance between crosslinks. A distance between crosslinks may be calculated based on geometric considerations of the number of functional groups and a distance between them. A crosslink in a crosslinked polymer matrix is a point that joins two polymers. In addition, entanglement may also increase effective crosslink density, especially if the hydrogel is formed from a system that has micellar type of solution structure. For instance, in a matrix formed by an electrophilic-nucleophilic chemistry, the precursors may be chosen to provide a calculated distance between crosslinks as in FIG. 8, depicting matrix 200, having multifunctional precursors 202, 204 with crosslinks 206 and covalent bonds 208 between precursors 202, 204. Precursor 202 has functional groups 210 that have been reacted with functional groups 212 of precursor 204. A calculated distance 214 is formed between crosslinks 206. The calculated distance is a useful metric for design and use of embolic materials and hydrogels. The calculated distance may be usefully described in terms of molecular weight (Mn). This calculated distance based on geometric considerations may also be referred to as a geometrically calculated distance. A free radical polymerization process with a multifunctional precursor may also have a calculated distance between crosslinks based on the geometry of the precursors.

A calculated distance between crosslinks decreases as a density of crosslinks increases. A calculated distance between crosslinks for an embolizing material and/or a hydrogel embolizing material may be, for example from 200 to 200,000; artisans will immediately appreciate that all ranges and values within this range are contemplated and supported, e.g., 200 to 250,000, 500 to 300,000, 500, 1000, 2000, 3000, 4000, 5000, 6000, 8000, 10000, 12000, 15000, 20000, 25000, 30000, 35000, 40000, 50000, 60000, 70000, 80000, 90000, 100000, 150000, and 200000 Daltons (Mn). Precursors with longer distances between crosslinkable sites form gels that are generally softer, more compliant, and more elastic relative to shorter distances. Thus an increased length of a water-soluble segment, such as a polyethylene glycol, tends to enhance elasticity to produce desirable physical properties. Thus certain embodiments are directed to precursors with water soluble arms having molecular weights in the range of 200 to 50000; artisans will immediately appreciate that all the ranges and values within the explicitly stated ranges are contemplated, e.g., 200, 400, 500, 600, 700, 800, 1000, 1200, 1500, 1800, 2000, 2500, 3000, 4000, 5000, 7000, 10000, 20000, 30000, 40000, 50000 Daltons (Mn).

The solids content and crosslink density of a hydrogel affects its mechanical properties and may impact its biocompatibility; a solids content for the hydrogel may be e.g., between about 2.5% to about 40%; artisans will immediately appreciate that all ranges and values between the explicitly stated bounds are contemplated. 2.5% to 25%, about 5% to about 15%, 2.5, 3.0, 4.0, 5.0, 6.0, 8.0, 10.0, 12.0, 14.0, 16.0, 18.0, 20.0, 22.0, 25.0, 30.0, 40.0% w/w.

Compression modulus is a measure of stiffness. It is a ratio of mechanical stress to strain in an elastic material when that material is being compressed and is measured in units of a compressive force per unit area/change in volume per unit volume. A high compression modulus material, such as a cyanoacrylate glue, is stiff and unyielding. Such materials are difficult to remove; for instance a surgical dissection of a tissue containing a mass of cyanoacrylate is difficult. A lower modulus provides a softer material. A modulus that is comparable to a modulus of a tissue further provides for a material that, if it swells after delivery, will not unduly distort or even break the blood vessel or other tissue. A distance between crosslinks that is relatively low provides for a stiffer material with a higher modulus and a distance between crosslinks that is higher provides for a relatively lower modulus providing a glass transition temperature below the usage temperature and/or the presence of a plasticizer such as water. A compression modulus of the embolic hydrogel preferably is from 5-200 kPa; Artisans will immediately appreciate that all ranges and values between the explicitly stated bounds are contemplated, including 10-100 kPa or 15-75 kPa.

Swelling is also useful for embolic materials, including hydrogels, which are measured at equilibrium weight conditions (EWC). Swelling is measured in an excess of aqueous solute without volume constraints: % swelling=[(Weight at EWC−Weight at initial formation)/Weight at initial formation]*100. A range of swelling from 20-80% is useful; artisans will immediately appreciate that all ranges and values between the explicitly stated bounds are contemplated, including 20, 40, 50, 60, 70, 80 or 40-80%.

Artisans that have read the Application will be able to make hydrogels with a combination of the preferred properties of swelling, compression modulus, and calculated distances between crosslinks, and can adjust a solids content and choice of precursor appropriately. Embolic materials that include at least one, or all, of the precursors chosen to be water soluble polymers are preferred, e.g., a PEG polymer and/or a peptide.

The hydrogels may be formed in a presence of further materials. Radiopaque agents may be used that are effectively inert in terms of covalent bonding with the hydrogel matrix. Solids content of a hydrogel refers to a dry weight of the matrix and does not include non-matrix materials, e.g., salts or radiopaque agents that are not covalently bonded to the matrix. Solids content can be calculated based on the concentrations and compositions of the precursors and their processes of crosslinking.

Gel time of a macromer or a functional polymer comprising a polymerizable group in a crosslinkable system is generally related to a time until the initiator is formed, a time to initiate polymerization of vinylic groups, and a polymerization time for the vinylic groups to react with each other to form a crosslinked system. The reaction is terminated mainly through re-combination. A gel time of less than 5 seconds is generally advantageous to form embolic materials in flowing blood, e.g., no more than 0.8, 1, 2, 3, 4, or 5 seconds. In applications wherein a relatively large volume of embolic material is desirable, e.g., embolizing lacerated vessels, shorter gel times may be useful.

Embolic components may be chosen to provide a cohesive embolic material, e.g., a cohesive hydrogel. Cohesiveness is a property referring to a tendency of the formed embolic to stick to itself in preference to the environment in which it is formed. A material that is formed in a silicone tube or a non-branched vascular tissue as a solid mass that is readily removable as a cohesive whole is a cohesive material. The embolic materials formed while in contact with vascular tissue in Examples 1-3 and 9 were observed to be cohesive and excised tissue could be manually squeezed to extrude the embolic hydrogel material out of the embolized blood vessels as a cohesive mass. The hydrogels were observed to be cohesive in plastic tubing in Examples 10-11, wherein the hydrogels were observed to form a single cohesive mass without sticking to the plastic or the catheter. Cohesiveness contributed to the easy removal of the delivery catheter in Examples 10-11 since the hydrogel tended to stick to itself in preference to the surrounding tissue and/or catheters. Cohesiveness is a property that is different than adhesivity, with adhesivity being a property of an adhesive adhering to materials other than the adhesive, e.g., an embolic that adheres to a tissue is adhesive.

The test results reported in Examples 10-11 are in contrast to other embolic agents, ONYX (a precipitating polyvinyl alcohol) and glue (n-butyl cyanoacrylate) may adhere to the catheter used to deliver them. This has been reported as being rendered permanently embedded in the embolic material and subsequently left in the main aorta. This adverse event may require surgery or treated with a maintained dose of antiplatelet agents, J Korean Neurosurg Soc. 2012 June; 51(6): 374-376; J Vasc Intery Neurol. 2015 July; 8(3): 37-41; Intery Neuroradiol. 1997 Mar. 30; 3(1):13-9. Epub 2001 May 15.

Embolic Compositions

Embolic compositions are delivered in a plurality of liquids that are combined to make the embolic material by reaction of the embolic components in the liquids to form an embolic material from a crosslinking reaction of a multifunctional precursor, with the term 'a precursor" meaning one or more chemical species of precursor. The embolic material may be a hydrogel or a non-hydrogel and may be biodegradable or non-biodegradable.

One of the embolic components comprises a multifunctional precursor. A concentration of the multifunctional precursor in a liquid as-prepared to deliver to embolic component ranges from 5-60% w/w. The term as-prepared refers to the concentration of the precursor in the liquid before it is delivered. These concentrations are applicable for the chemical schemes described herein, including polymerizations initiated by a redox reaction and electrophile-nucleophile chemistry. One or more multifunctional precursors may be chosen with a structure as described herein, with the desired structure of a hydrogel or other embolic material being as described herein.

Embodiments that use a polymerizations with redox initiated reaction provide a liquid that comprises the multifunctional precursor and another liquid that comprises an initiator. A reductant is provided in a liquid that is separate from the peroxide. Precursors, functional groups, reductants, and initiators and their structures and concentrations are chosen as described herein. The liquids are mixed to react the components.

Embodiments that use an electrophilic-nucleophilic chemistry provide one liquid that comprises a multifunctional precursor at a concentration of 5-60% w/w that comprises an electrophilic functional group and a multifunctional precursor at a concentration of 5-60% w/w that has a nucleophilic functional group. A second liquid is provided that provides for a shift of the mixed liquids to a pH that allows reaction of the functional groups with each other. Precursors, functional groups, and their structures and concentrations are described in detail herein. In the case of a succinimide group, the liquids provide a pH of 7-12 when combined; artisans will immediately appreciate that all ranges and values between the explicitly stated bounds are contemplated, e.g., 7.0, 7.2, 7.4, 8.0, 8.5, 9.0, 9.5, 10.0, 11.0 or 12.0. One or more salts or buffers may be used in one or both liquids to provide the desired pH.

The embolic components may be present with one or more contrast agents, e.g., radiopaque agents. Contrast agents may include iodinated contrast or a radiopaque metal or derivative thereof. Amounts in 10% to 70% w/w are generally useful; Artisans will immediately appreciate that all ranges and values between the explicitly stated bounds are contemplated. 10, 20, 30, 40, 50, 60% w/w.

The contents of the liquids containing the embolic components are provided for delivery in a pharmaceutically acceptable form, meaning highly purified and free of contaminants, e.g., pyrogens.

Embolization Systems and Methods

An embodiment of an embolization system comprises a first fluid supply containing a first liquid that comprises a water soluble polymer comprising a plurality of vinylic functional groups and a co-initiator, a second fluid supply containing a second liquid that comprises a polymerization initiator, and a catheter adaptor connectable to the first fluid supply for delivery of the first liquid to a first catheter lumen and connectable to the second fluid supply for delivery of the second liquid to a second catheter lumen. Embolic components may be chosen per the guidance herein, e.g., precursors (a term that includes multifunctional precursors), systems that use redox polymerizations, systems that use electrophilic-nucleophilic chemistries. For instance, one embodiment is a multiple lumen catheter having a first lumen and a second lumen for delivery of fluid; a first fluid supply fluidly connectable to the first lumen for delivery of a liquid through the first lumen to a site in vivo, with the first fluid supply containing a first liquid that comprises a first embolic component; a second fluid supply fluidly connectable to the second lumen for delivery of a liquid through the second lumen to a site in vivo, with the second fluid supply containing a second liquid comprising a second embolic component. A coaxial catheter adapter may be used to provide desired connectivity. In embodiments using a polymerization initiated by redox, one of the embolic components is a precursor, e.g., multifunctional precursor, and a reductant and is present in the first liquid or the second liquid and the other embolic component is an peroxide. In an electrophilic-nucleophilic chemistry one of the embolic components comprises a first precursor, e.g., multifunctional precursor, comprising an electrophilic functional group and the other embolic component comprises a second multifunctional precursor comprising a nucleophilic functional group. Accordingly, the first liquid can be chosen to provide a multifunctional precursor and the second liquid can be chosen to provide an initiator, or vice versa. Or the first liquid can be chosen to provide a multifunctional precursor comprising electrophilic functional groups and the second liquid can be chosen to provide a multifunctional precursor comprising nucleophilic functional groups, or vice versa. The multiple lumen catheter may be coaxial or as otherwise described herein.

Catheters may be introduced into a vasculature or other area of a patient using known techniques, e.g., Seldinger or modified Seldinger.

Delivery of embolic components is preferably performed with real-time imaging. Real-time imaging includes angiography, fluoroscopy, MRI, computed tomography, computed tomography cone beam. The term real-time refers to an instant visualization and techniques that involve a short delay in imaging, for instance a delay of up to about 5 minutes.

Delivery may be by way of a bolus, slow continuous delivery or using puff technique. The term bolus is used to herein to refer to a continuous administration of a rate of about 0.1-1.0 ml/s whereas the slow continuous delivery is delivered at about at up to about 0.1 ml/s. The term puff is used herein to refer to a stepwise process of embolic component administration. This stepwise process comprises a plurality of steps for administering a total dose of an embolic composition in a series of partial doses, with each step comprising administering a dose portion separated by a period of time for assessment of the embolic effects of each dose portion. After each partial dose the effects are observed and another step comprising administration of a partial dose and a delay is repeated until embolization is complete. In general, a total dose is from 0.1-50 ml, a delay from 1 to 60 seconds is suitable, and 2-50 steps (partial doses) are suitable. Artisans will immediately appreciate that all ranges and values between the explicitly stated bounds are contemplated: 0.1, 0.2, 0.3, 0.4, 0.5, 1, 2, 3, 4, 5, 6, 7, 8, 9, 10, 15, 20, 25, 30, 35, 40, 45, 50 ml; or 1, 2, 3, 4, 5, 10, 20, 30, 40, 50, 60 seconds; or 2, 3, 4, 5, 6, 7, 8, 9, 10, 15, 20, 25, 30, 40, or 50 partial doses. For example, an embolic treatment of a hypervascular tumor (benign or cancerous) a total dose is generally from 0.1-2 ml, partial doses are from 0.01 to 1 ml, and a delay of 1-10 seconds is suitable. And, for example, embolization of vascular areas that require a dose of no more than 5 ml are generally treatable in 2-10 steps with partial doses of 0.1-1.0 ml with a delay of 1-10 seconds. And for example, hemostasis applications, for instance a lacerated blood vessel, can require a volume of embolic composition ranging from, for instance, 1-50 ml that is administered in 2-10 partial doses. In all cases a longer delay may generally be used but is not clinically helpful. Artisans will immediately appreciate that all ranges and values between the explicitly stated bounds are contemplated for the partial doses, e.g., 0.01, 0.02, 0.025, 0.05, 0.1, 0.15, 0.2, 0.25, 0.3, 0.5, 0.7, 0.8, 1, 1.2, 1.5, 1.8, 2 ml.

Embolic components that react quickly with each other to make the embolic material are useful. A quick reaction in combination with a dilutive effective of flowing blood or other dilutive effects is believed to usefully promote the formation of embolic materials as domains. Accordingly, embodiments include delivering two or more fluids that collectively comprise two or more embolic components to provide a quick reaction time according to a gel test as described herein of no more than 5 seconds; artisans will immediately appreciate that all ranges and values between the explicitly stated bounds are contemplated: 0.1, 0.2, 0.3, 0.4, 0.5, 0.6, 0.7, 0.8, 0.9, 1, 1.1, 1.5, 2, 2.5, 3, 4, and 5 seconds or 0.05 to 3 seconds. Longer reaction times are also useful, e.g., from more than 5 seconds to 600 seconds, as measurable by an in vitro a gel time test; Artisans will immediately appreciate that all ranges and values between the explicitly stated bounds are contemplated. 5, 10, 15, 20, 30, 60, 90, 120, 150, 180, 210, 240, 270, 300, 400, 500, and 600 seconds.

Dilutive effects were observed to be significant. Some dilution was unexpectedly useful but an excess of dilution prevented embolization. The dilution problem, however, was turned to an advantage by its use as a design factor to minimize the risk of embolization in off-target tissue. The embolic components and the liquids used to deliver them may be chosen to deliver components that can be diluted when delivered in vivo and nonetheless form an embolic material. Embolization can be observed in vivo by observing whether or not delivery of the embolic compositions block blood flow to a target area. It is also useful to define a dilutive capacity of the embolic components in terms of the in vitro gel time test. Liquids are prepared that are for delivery through the catheter lumens; these contain the embolic components and other materials contemplated for delivery at the appropriate concentrations. These liquids are tested with the in vitro gel time test at a 1:1 ratio. Embodiments of dilutable embolic components include components that form embolic materials at a nominal concentration (concentration after being mixed) but fail to form an embolic material when diluted by 300% v/v, or alternatively, by a value from 250-500% v/v; Artisans will immediately appreciate that all ranges and values between the explicitly stated bounds are contemplated: 250, 300, 350, 400, 450% v/v. A dilution of embolic components by 100% v/v decreases concentration of the components by 50%. For instance, delivery of 100 µl of a first component and 100 µl of a second component (i.e., delivered at a ratio of 1:1 v/v) is diluted 100% by addition of a 200 µl volume and is diluted by 200% by addition of a 400 µl volume. Further, instead of using failure to form a gel in vitro as a criterion, a significantly delayed gel time may be chosen, e.g., wherein a predetermined amount of dilution (e.g., 250-450% v/v) prevents formation of the embolic material in vitro within 0.3-30 minutes; artisans will immediately appreciate that all ranges and values between the explicitly stated bounds are contemplated, such as 20, 30, 60, 120, or 600 seconds, 15, or 30 minutes.

The embolization systems may be provided as a kit. A kit has the embolic components and may have one or more of: an adaptor that cooperates with one or more catheters and fluid supplies intended for use with the kit; a fluid supply for a first embolic component, a second fluid supply for a second embolic component, one or more containers of water or other aqueous solution to use with one or more embolic components, a radiopaque material, a pump, or a syringe or syringes (one or two-barreled). A preferred embodiment is a kit that provides at least the embolic components, an inner catheter for a coaxial catheter system, and a coaxial catheter adapter. Embolic components may be chosen using the guidance provided herein. Kits may include instructions to prepare liquids that contain one or more components at a predetermined concentration. The embolic components may be provided, e.g., ready to use for delivery through a catheter, in aqueous solution, as a liquid, as a solid, as a ready-to-use solution, or as a concentrated solution to prepare the contents of a liquid to be delivered via a catheter. For instance, a component provided as a solid may be prepared by a user at a desired concentration by addition of a predetermined amount of liquid or by combining the solid with a pre-prepared volume of solution that, upon addition, provides the desired concentration of the component.

An example of a coaxial catheter adaptor is a Tuohy-Borst adaptor. The choice of connectors may be used to help guide the user in the choice of suitably sized catheters. And/or the connectors of the adaptor may be specifically sized for a particular fluid supply so that users can only connect a fluid supply to an intended connection point and thus deliver a particular embolic component only through a desired catheter and/or catheter lumen.

Uses

Examples of uses of a multi-lumen catheter such as a coaxial catheter and/or embolization components are: for treatment of a disease, pathological condition, or in a vascular indication, including a treatment of a tumor, a hypervascular tissue, a vascular abnormality, a hypervascular tumor, a vascular laceration, a blood vessel, an organ, a tumor, a fibroid, a cell mass, an aneurysm, an aortic aneurysm, an abdominal aortic aneurysm, a peripheral aneurysm, for hemostasis, a venous laceration, or a tissue requiring treatment, or other vascularized tissue to be embolized. This use may be independent of, or in combination with, further methods or devices such as embolization coils, hemostatic devices, hemostatic agents, or the like. The term tumor is broad and includes fibroids, cysts, lipomas, and a hypervascular tumor, cancerous or benign. A multi-lumen catheter as described herein is introduced into a vasculature and positioned at a position proximal to the tumor or other tissue in the vasculature. Positioning may be made with or without use of a guidewire as known to persons of skill in these arts. In a slidable coaxial catheter embodiment an outer catheter is positioned and an inner catheter is passed through the outer catheter and the tip is positioned as desired with the inner catheter distal tip located distally relative to a tip of the outer catheter, with an offset distance being chosen as described herein. Fluids containing embolic components and other substances as desired are passed through the lumens and out of the catheters where the components react with each other to form an embolic material, e.g., a hydrogel. Concentrations of the components, rate and volumes of delivery, doses or partial doses, and reaction chemistries may be chosen as described herein. The choice of components may be made in light of a desired hydrogel composition, local blood flow rates or other conditions, and the desired diameter of blood vessel for embolization e.g., from 4 μm to 15 mm. A total volume for treatment of a tumor is chosen in light of the size of the tumor and may range from 0.2-2.0 ml.

In a multi-lumen catheter, the first lumen and the second lumen may be independently selected to range from 0.005 to 0.2 inches diameter. When the multiple lumen catheter comprises an inner tube and an outer tube coaxially surrounding the inner tube, with the first lumen being in the inner tube and the second lumen being an annulus formed between the inner tube and the outer tube, the inner tube may be selected to have an outer diameter ranging from 0.005 to 0.1 inches, and the outer tube may be selected to have an inner diameter ranging from 0.01 to 0.2 inches, with the inner tube outer diameter being selected to pass through the outer tube lumen. Certain embodiments of a coaxial catheter provide for the inner tube having an inner diameter to provide a cross-sectional area from 0.005 to 0.2 in$^2$ and the annulus having a cross-sectional area from 0.00005 to 0.005 in$^2$, with the inner tube outer diameter being selected to pass through the inner diameter of the outer tube lumen.

Patents, patent applications, and other publications referred to herein are hereby incorporated by reference herein for all purposes, with the present disclosure being controlling in case of conflict. Embodiments include features set forth herein as be combined with each other, e.g., catheters, embolic components, precursors, initiators, reductants, and hydrogel structures.

EXAMPLES

Example 1: Rabbit Renal Embolization, Targeted Embolization

A New Zealand white rabbit was used to test the effectiveness of a catheter system to deliver, and the embolic components to form, an embolic material in vivo. The catheter system was comprised of two single lumen catheters co-axially anchored to form dual channels for independent delivery of two fluids that, when combined, create a rapid gelling embolic that can penetrate deep into the vascular anatomy. The embolic material was a hydrogel formed by the introduction of two fluid streams: one containing a diacrylate polyethylene glycol combined with an iron compound and another consisting of a peroxide in solution with an iodinated contrast agent.

The catheter system was an outer and inner catheter coupled together by a Tuohy-Borst adapter with side port. The outer catheter was a Boston Scientific Renegade HI-FLO microcatheter having an inner lumen of 0.027 inches. The inner catheter was a stainless-steel coil-reinforced polyamide shaft having inner and outer diameters of 0.014 inch and 0.017 inch, respectively, and having a strain relief and hub assembly adhered to the proximal end. The Touhy Borst adapter with side port was connected to the hub of the outer catheter per standard EN/ISO luer terminations, and the inner catheter was passed through the compression fitting of the Tuohy-Borst adapter. Once introduced into the compression fitting, the inner catheter was advanced until its tip was in position. The inner catheter was then secured within the Tuohy-Borst adapter by actuating the compression fitting around the strain relief of the inner catheter.

A first liquid was prepared that contained 30% (w/w) of linear diacrylate polyethylene glycol (3.4 kg/mol, Mn) in solution with 0.88% (w/w) of ferrous gluconate (FeG) aqueous. A second liquid (initiator solution) included 1000 ppm of tertbutyl hydroperoxide (TBHP) in in solution with iodinated (iopromide) contrast media, ULTRAVIST 300. Upon a 1:1 v/v delivery, the resultant formed hydrogel embolic had a nominal 15% w/w PEG.

Following induction of general anesthesia and preparation, access to the dorsal aorta in the rabbit model via a surgical cut-down was performed. The dorsal aorta was punctured using a 21 gauge needle followed by introduction of an 0.018 inch guidewire. Under fluoroscopic imaging the catheter delivery system was put into place by the following steps. An angiography sheath was placed as a conduit for subsequent device placement including a guide catheter. The outer catheter was introduced through the guide catheter and positioned in the right renal artery. A baseline angiogram of the target kidney vasculature was performed. The inner catheter was co-axially inserted through the Tuohy-Borst adapter attached to the microcatheter hub and tracked until approximately 5 millimeters protruded from the outer microcatheter tip. 1 mL syringes, one filled with the prepolymer and one with the initiator solution, were connected to the proximal hubs of the catheter system. The syringe containing the prepolymer solution was connected to the inner catheter, and the initiator solution was connected to the Tuohy-Borst side port for delivery through the annular gap formed between the inner catheter outside diameter and the outer microcatheter inside diameter. The syringes were secured in an injection cradle to allow for tandem delivery of both solutions. Through this catheter delivery system and with equal delivery (1:1 v/v) of both solutions, a total of 0.8 mL of embolic volume was delivered in a single bolus over a few seconds, with the embolic forming upon delivery. A follow-up digital subtraction angiogram (DSA) was performed and confirmed that the formed polymer created a target embolic in the renal vasculature, without delivery or migration of formed hydrogel to non-targeted areas.

The rabbit was euthanized and the target kidney harvested. With the aid of a dissecting microscope, the right kidney was sectioned and characterized. The gel was stained using trypan blue to enhance the contrast between native tissue and hydrogel embolic. Gel was identified to comprehensively occlude the target vessels with gel present in large (at least 15 μm diameter) and small vessels (less than 15 μm in diameter).

Example 2: Rabbit Renal Embolization, Dilution Sensitivity

In the same study as Example 1, the left kidney was embolized using same materials and delivery system as Example 1. This experiment intentionally delivered in proximity to a cranial mesenteric artery branch of the left renal artery. Through the catheter delivery system a total of 1.2 mL of embolic volume was delivered in a single bolus over a few seconds, with the embolic forming immediately upon completed delivery. During injection, it was observed that the excess injection volume flowed into the cranial mesenteric artery yet did not polymerize due to increased dilution due by flowing blood, as confirmed fluoroscopically. Post-mortem assessment of the target tissue again showed extensive embolization with hydrogel filling large and small vessels (less than 15 μm).

Example 3: Rabbit Renal Embolization, Puff Delivery Technique

In the same model as Examples 1 and 2 but in a separate study, the kidneys of a rabbit were embolized using two techniques, bolus and puff. Using the same catheter system set-up as prior noted yet replacing the outer catheter with a Terumo PROGREAT Microcatheter System, embolization procedures were performed under fluoroscopic imaging. For this study, the prepolymer solution contained 12% (w/w) of linear diacrylate polyethylene glycol (10 kg/mol) in solution with 0.88% (w/w) of ferrous gluconate (FeG) aqueous. The initiator solution included 2830 ppm of TBHP in solution with iodinated contrast media, ULTRAVIST 300. Upon a 1:1 delivery, the resultant formed hydrogel embolic consisted of a nominal 6% PEG.

The left kidney procedure applied a bolus delivery of 0.7 mL over a few seconds, consistent with prior examples but with differing embolic formulation. The right kidney was embolized using a puff technique in which a series of approximately 0.2 mL injections of embolic volume was delivered in approximately 1 second intervals with about 1-2 second delays in delivery. The right kidney was embolized with eight puffs of 0.2 mL for a total of 1.6 mL of embolic volume. DSA confirmed occlusion of both kidneys. Post-mortem assessment of the target tissue again showed extensive embolization in both kidneys, demonstrating the utility of both techniques (bolus and puff) for delivery of the two-part hydrogel embolic.

Example 4: In Vitro Testing, Gel Time Test

Gelation experiments were performed to characterize the time required to form a hydrogel upon combination of a prepolymer and initiator solution. The term "in vitro gel time test" refers to a test performed using the methods of this example, with two liquids being mixed and the time to gelation being recorded as described below. The test system included a basic set-up consisting of a stirrer plate with a 5 mm thick glass plate spacer (to reduce magnetic force), disposable borosilicate glass culture tubes (12×75 millimeters) each containing a TEFLON-coated flea stirrer bar (7×2 millimeters) and suspended from a ring stand, a digital microscope camera connected to a computer for image collection, and two pipettes and tips in a suitable range to deliver 100 microliters (μl).

Using a pipette 100 μl of prepolymer solution, containing 12% PEG and 0.88% (w/w) FeG aqueous, was added to the glass culture tube with a flea stir bar spinning with the stirrer plate set at 1000 rpm. The digital camera was started using the computer control to record the gelling event. A 100 μl of initiator solution, 1000 ppm (w/w) TBHP with iodinated contrast agent (ISOVUE 300), or with an initiator and contrast agent with concentrations as otherwise indicated), was then added to the glass tube test environment. The camera recording was stopped when the stir bar halted due to gel formation or, if the stir bar did not stop, when the gel had visibly formed as observable by a reduction in the free liquid level in the tube, and a digital record of the gelling event was captured. Average results from the gel time test for a range of linear diacrylate PEG polymers at varying polymer concentration are presented in Table 1 below.

TABLE 1

Gel times for various water soluble polymer concentrations and MWs

| Molecular Weight (kg/mol) | Final Nominal PEG Concentration (% w/w) | | |
|---|---|---|---|
| | 15 | 10 | 7.5 |
| | Gel Time (s) | | |
| 3.4 | 1.7 | 2.5 | 4.2 |
| 5 | 1.4 | 2.0 | 2.6 |
| 8 | 0.9 | 1.6 | 2.2 |
| 10 | 0.8 | 1.1 | 1.5 |

To evaluate the impact of TBHP and FeG concentration on gel time, the polymer was held constant for a subsequent evaluation. The polymer was a 3.4 kg/mol (Mn) diacrylate PEG at 15% w/w final nominal concentration and was tested with varying concentrations of FeG and TBHP. The average resultant gel time is presented in Table 2 below, demonstrating the effect of FeG and TBHP concentrations on gel time.

TABLE 2

Gel times for various peroxide and reductant concentration

| FeG Concentration, % w/w | TBHP Concentration (ppm w/w) | | |
|---|---|---|---|
| | 1000 | 2000 | 3000 |
| | Gel Time (s) | | |
| 0.88 | 1.7 | 0.8 | 0.6 |
| 1.32 | 1.0 | 0.6 | 0.4 |
| 1.76 | 1.0 | 0.6 | 0.3 |

Example 5: In Vitro Testing, Dilution Sensitivity

This example highlights the embolics' dilution sensitivity, as dilution retards gelation and, at a high enough volume, prevents it. The materials and methods of Example 4 were used unless otherwise indicated. The tested prepolymer solution was 10 kg/mol diacrylate (Mn) PEG at 12% w/w combined with 0.88% w/w FeG. Two experiments were conducted with different initiator solutions, with starting concentration of 500 ppm (w/w) or 2830 ppm (w/w) of hydrogen peroxide ($H_2O_2$) and TBHP, in respectively, in ULTRAVIST 300. Noting a 1:1 v/v delivery, the baseline nominal PEG concentration was 6% after dilution with PBS. For each initiator type, experimentation included equal part dilution of prepolymer and initiator solutions to achieve a final nominal PEG concentration of 5, 4, 3, and 2% w/w in addition to the baseline 6%. Average gel time results are presented in the table below.

TABLE 3

Dilution sensitivity for various hydrogel precursor, initiator, and reductant concentrations.

| Peroxide | Final Nominal PEG Concentration (% w/w) | | | | |
|---|---|---|---|---|---|
| | 6 | 5 | 4 | 3 | 2 |
| | Gel Time (s) | | | | |
| H202 | 0.5 | 0.8 | 11 | No gel | Not Tested |
| TBHP | 0.7 | 1.2 | 2.2 | 3.5 | No gel |

Example 6: In Vitro Testing, Dilution Sensitivity

Gel time tests according to Example 4 were used to test dilution sensitivity. Precursor were prepared as follows.

Polymer precursor, 12% PEG/1% FeG: 409 mg 10 kg/mol PEG diacrylate (PEGDA) and 3 ml 1.13% FeG(aq).

Initiator precursor, 2000 ppm TBHP: 9.45 g ULTRAVIST 300 and 1.82 g 1.24% TBHP(aq).

For dilution sensitivity the polymer precursor were diluted with PBS in the following volume before being tested for gel time; Polymer precursor: PBS ratios; 80:20; 60:40 and 40:60 corresponding to nominal concentrations of 4.8, 3.6, 2.4% Nominal PEG concentration in any formed gel, respectively. Undiluted samples (12% PEG) correspond to a nominal 6% PEG concentration. The TBHP-containing solution (2000 ppm when undiluted) was diluted to match the dilution of the PEG containing precursor.

TABLE 4

Dilution sensitivity 12% PEGDA-containing solution mixed 1:1 v/v with TBHP-containing solution. Two individual samples were tested.

| | Gel time, seconds | |
|---|---|---|
| Sample, ratio | Mean | Std Dev |
| #1, 80:20 | 0.728 | 0.023875 |
| #1, 60:40 | 1.512 | 0.08228 |
| #1, 40:60 | 2.42 | 0.568727 |
| #2, 80:20 | 0.73 | 0.043012 |
| #2, 60:40 | 1.486 | 0.031305 |
| #2, 40:60 | 2.29 | 0.149499 |

Example 7: Gel Time Comparison for Bifunctional and Tetrafunctional Polymer Precursors A gel time test was performed according to Example 4. The following precursors were prepared using 20 kg/mol PEGDA (Mn) or 20 kg/mol 4 arm PEG tetraacrylate (Mn).

Polymer precursors were prepared to have 1% FeG when mixed.

Initiator precursor was 2000 ppm TBHP in ULTRAVIST 300 contrast agent. The polymer precursor and initiator precursors were mixed 1:1 v/v for the test. Concentrations before mixing are shown in the table below.

TABLE 5

Gel time for 20k bifunctional PEGDA and 20k branched PEG tetraacrylate

| | Gel time, seconds | |
|---|---|---|
| Composition | Mean | SD |
| #1. 12% 20k linear PEGDA, 2.6% FeG | 0.422 | 0.034205 |
| #2. 12% 20k linear PEGDA,, 1% FeG | 0.55 | 0.057879 |
| #3. 8% 20k linear PEGDA, 1% FeG | 0.77 | 0.055678 |
| #4. 12% 20k 4arm PEG tetraacrylate, 1% FeG | 0.404 | 0.035071 |
| #5. 8% 20k 4arm PEG tetraacrylate, 1% FeG | 0.45 | 0.029155 |
| #6. 6% 20k 4arm PEG tetraacrylate, 1% FeG | 0.604 | 0.011402 |

Example 8: Two-Part Electrophilic-Nucleophilic Functionalized Precursors for Embolization A polymer precursor of a succinimidyl functional branched PEG and trilysine was prepared in an acidic aqueous buffer and delivered from a first syringe through an inner catheter of a coaxial catheter system, with the PEG being present at 19% w/w and the trilysine stochimetrically matched. An alkaline acceleration solution comprising a contrast agent and alkaline salts was delivered from a second syringe through the annular gap between the inner catheter and an outer catheter. The delivery was made at a 1:1 v/v ratio of polymer precursor:alkaline acceleration solution. The alkaline acceleration solution had a pH 10.9 and acted as an accelerator to crosslink the PEG and trilysine upon mixing. This embolic system gel time was 0.4 s.

This formulation was evaluated an in vivo porcine model. Kidney and liver embolizations were successfully carried out. The delivery system of Example 1 was used. A 1:1 v/v mixture of the PEG precursor and a trilysine solution provides a nominal PEG concentration of 9.5%.

TABLE 6

Polymer precursor components packaged in a 10 cc syringe.

| Component | Molecular weight/Structure | Manufacturer | Amount/syringe |
|---|---|---|---|
| 4arm PEG SGA* | 40 kg/mol | JenKem Technology USA, Plano TX, | 756 mg |
| Trilysine salt | H-(Lys)3-OH, Acid salt | Bachem, Torrance CA | 30 mg |

*Succinimidyl Glutaramide (w/pentaerythritol core)

TABLE 7

Solution for PEG packaged in a 10 cc syringe.

| Component | Composition | Amount/syringe |
|---|---|---|
| Acidic buffer solutione | 0.1M $CH_3COONa$, 1 mM HCl | 3334 mg |

TABLE 8

Alkaline Contrast Agent packaged in a 10 cc syringe.

| Component | Composition | Manufacturer | Amount/syringe |
|---|---|---|---|
| Alkaline Contrast Agent, 0.3 Me | $Na_2HPO_4$ | Spectrum Chem., New Brunswick NJ | 426 mg |
| | $Na_2CO_3$ | Sigma Aldrich, St. Louis MO | 318 mg |
| | OMNIPAQUE 300 | GE Healthcare | 13.5 g |

Figure 9:
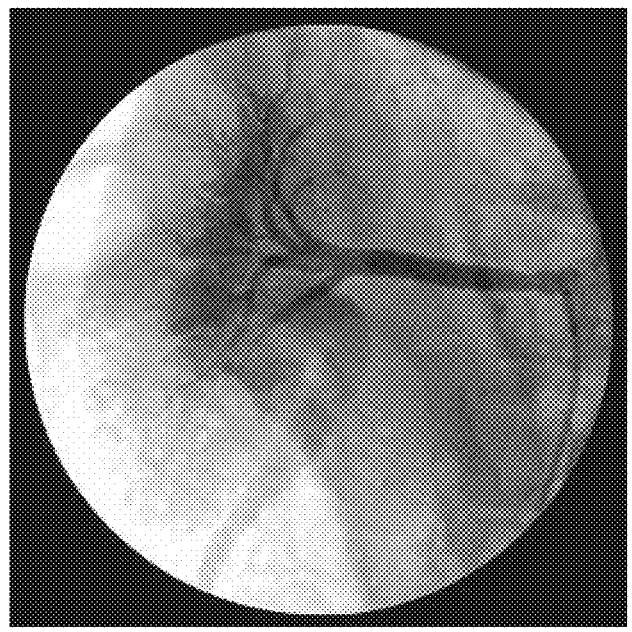
FIG. 9 is a baseline angiogram of a right kidney as described in Example 9.

Example 9: Embolizations with Electrophilic-Nucleophilic Functionalized Precursors The two-part electrophilic-nucleophilic functionalized precursor system of Example 8 was used, with further changes being described in this Example. The right kidney was accessed and the baseline angiogram of the liver was taken, see FIG. 9. No abnormalities were observed in the target vasculature.

The catheter was positioned to the most caudal portion of the right kidney. 1.8 ml of the combined solutions was delivered by puff technique without any observed embolization.

Figure 10:
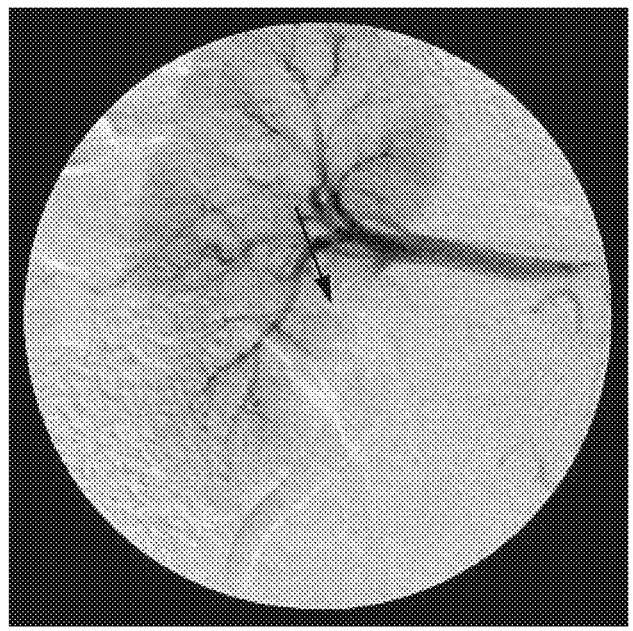
FIG. 10 is a subtraction angiogram in the most caudal portion of the right kidney as described in Example 9, with the catheter tip indicated by the arrow.

The precursor solutions were reformulated to reduce dilution sensitivity, by which the polymer concentration in the PEG solution was increased from the initial 19% (as in Example 8) to 23% (w/w). 1.9 ml (total, combined) of the two precursors was delivered and embolization was achieved, FIG. 10, with the arrow indicating the tip of the catheter.

Figure 11:
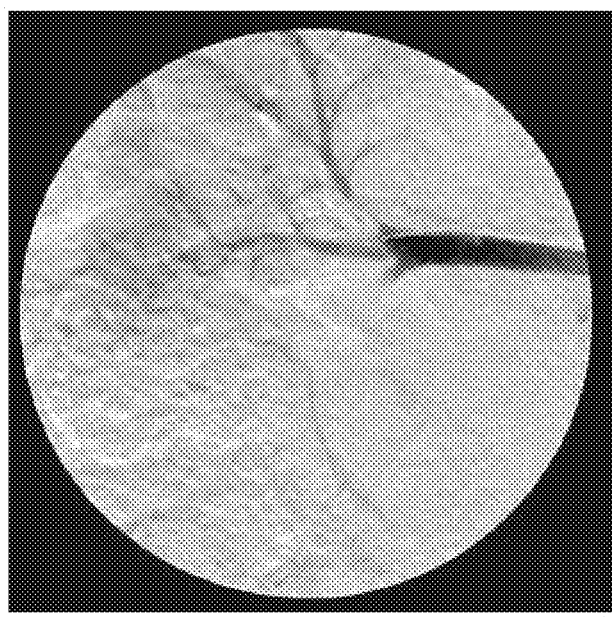
FIG. 11 is an image showing an embolized cranial artery in the caudal pole with catheter gel encasing and non-target cranial partial demonstrating complete embolization.

The catheter was moved to the cranial artery in the caudal pole and the same 2-part embolic was prepared (with the 19% PEG concentration). Initially 0.9 ml (total, combined) of embolic was delivered without achieving stasis. Another 1.2 ml was delivered and embolization was achieved, FIG. 11.

Figure 12:
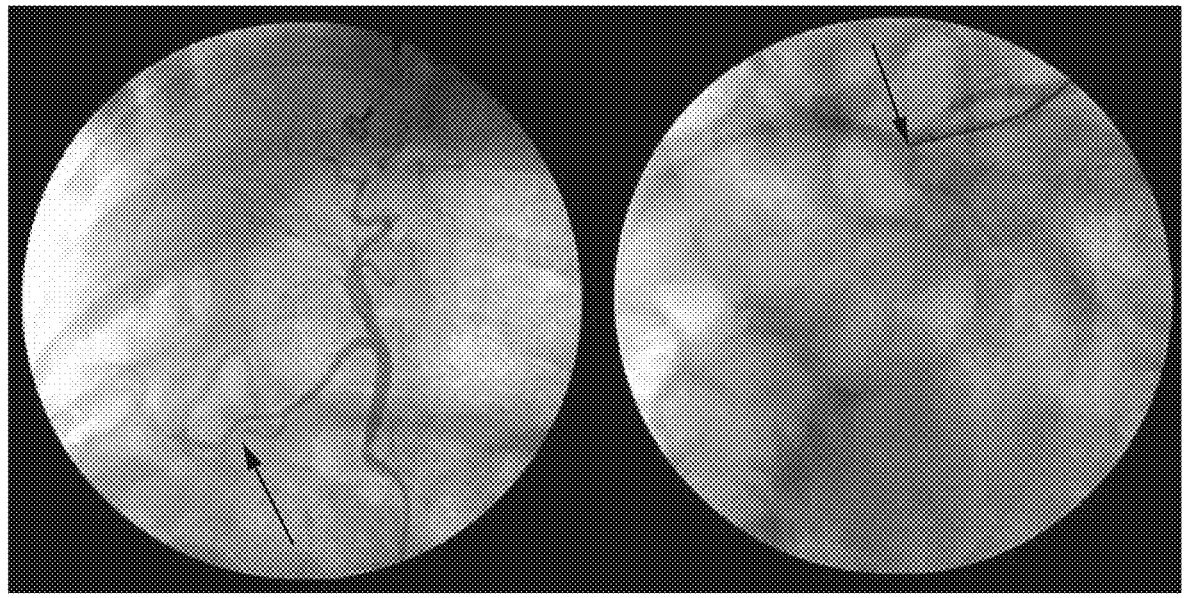
FIG. 12 is a liver baseline angiogram and catheter placement for delivery of an embolic into the right lateral lobe of the right kidney as described in Example 9, with the catheter tip indicated by the left-side arrow while right-side arrow indicates the position where the catheter tip was placed at the time of delivery.
Figure 13:
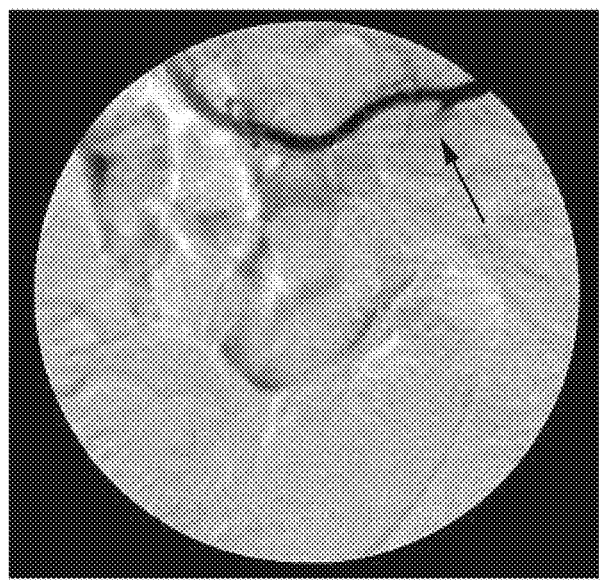
FIG. 13 is an embolized liver target vasculature, with the catheter tip indicated by the arrow.

The liver was accessed and the base angiogram of the liver is shown in FIG. 12. No abnormalities were observed in the target vasculature. The liver was embolized using the two-part electrophilic-nucleophilic functionalized precursor system with a 19% PEG solution. 1.2 ml of embolic agent (puff technique) was used to achieve embolization. An angiogram confirmed the embolization achieved of the target vasculature only as shown in FIG. 13.

Example 10: Catheter Pull Out Force

A test procedure was used to measure that force required to pull a catheter from an embolic material. In brief, a gel was intentionally formed around the catheter and an INSTRON tensile strength tester was used to measure a force required to pull the catheter from the gel, with the INSTRON operated at 500 mm/min, as per ISO 10555-1: 2013(E).

A length of tubing (PVC tubing ¼"×⅛", Durometer 65 A) was connected to a distal opening of a Tuohy Borst adaptor. A coaxial catheter assembly was prepared (2.8 French catheter, 20 cm and 1.7 French catheter, +20 cm) with the inner catheter extending 5 mm beyond the outer catheter and secured to each other. The distal end of the microcatheter assembly was passed through the Tuohy Borst adaptor and into the length of tubing, with the distal end of the assembly positioned 4 cm beyond the compression feature of the Tuohy Borst. The adapter was sealed around the coaxial catheters. A double barreled syringe, loaded with a first and a second precursor, was secured to the side port of the ad Touhy with a static mixing element between the syringes and the Tuohy. A total volume of 1.4 cm was injected into the set-up, where it formed a gel from the valve on the adaptor and covered the catheter assembly and extended beyond the distal tip of the assembly. In this fashion, the length of the catheter assembly in contact with the gel was carefully maintained throughout the experiments to be a length of 4 cm. After the gel was formed, the two barreled syringe and static mixing element were removed from the side port and the valve on the Touhy was loosened so that the valve did not apply a force to the catheter assembly. The proximal end of the catheter assembly and the Tuohy Borst adaptor were firmly secured to the tensile grips of the INSTRON device, operating at crosshead speed of 500 mm/min, as per ISO 10555-1:2013(E). Force and normalized force (for embedded length) was collected with average results of 1.07N and 0.27N/cm, respectively.

Example 11: Cohesiveness

The gels described in Example 10 were further evaluated for cohesivity. The catheter assemblies were pulled from the gels under the conditions described and checked with the naked eye under ambient light to see if any gel was visible on the catheter. No residual gel was observed.

Example 12

Figure 14:
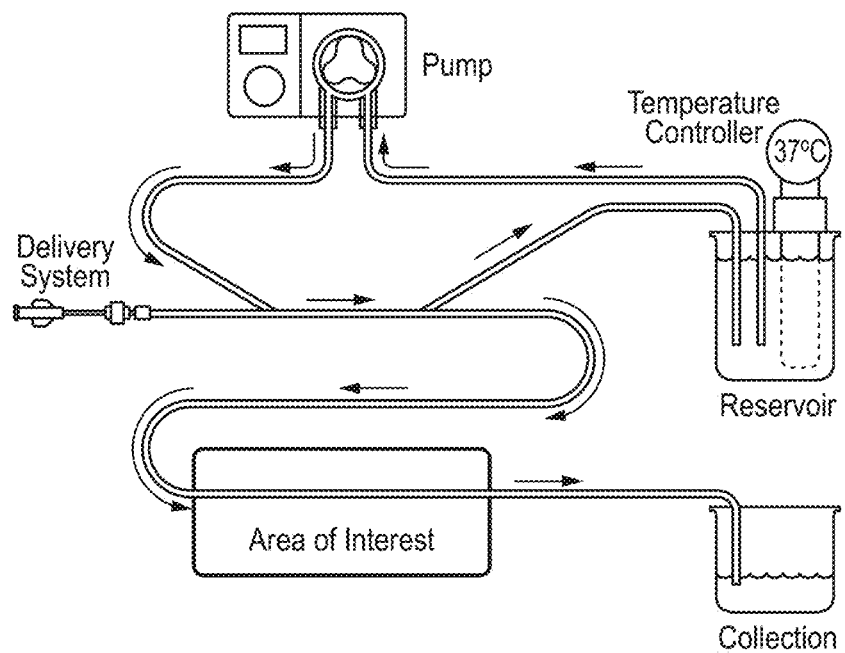
FIG. 14 is a schematic of a flow loop used for certain embolization studies.

Referring to FIG. 14, a polyvinyl tubing (1.0 mm-4.78 mm ID.) loop was created with an inlet in a source of 37.1° C. water and joined with a Tuohy Borst connector to provide access to a coaxial catheter delivery system. The outer catheter was a Terumo PROGREAT 2.8F microcatheter and the inner catheter has an OD of 1.7F, and an ID of 0.016 in. A dual barreled syringe was connected to the coaxial catheter. A barrel containing 12% PEG and 0.88% ferrous gluconate was connected to the inner catheter and a barrel containing 2830 ppm TBHP in ISOVUE 300. A small amount of green dye was added to PEG/FeG solution for visualization. The indicated area of interest in FIG. 14 was filmed with a video camera.

The coaxial catheter was positioned at the upstream end of the area of interest in the tubing. The peristaltic pump was operated to create a flow rate of 50 ml/min at the area of interest. The dual syringe was manually operated to dispense the embolic components into the tubing at the area of interest. Several puffs (meaning, in this context, about 100-500 µl) of the components were dispensed and it was observed that there was no formation of an embolic material.

Figure 15:
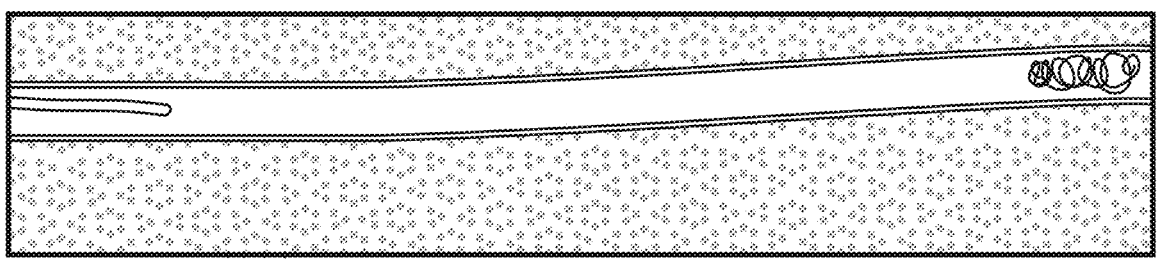
FIG. 15 is an image of the area of interest in the flow loop of FIG. 14, with a catheter releasing embolic components and dye into a flowing fluid that passes over a medical coil.
Figure 16:
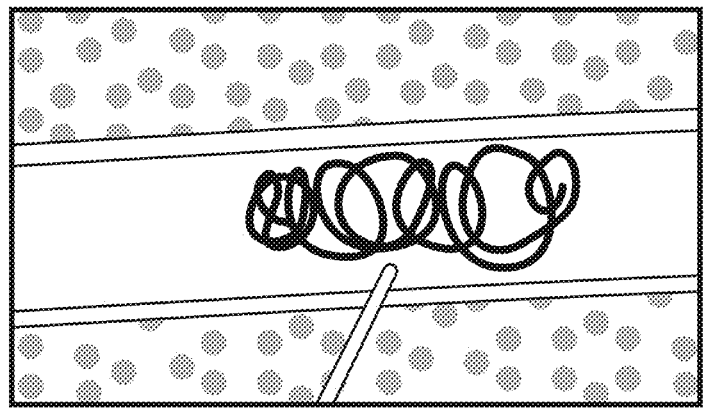
FIG. 16 is an image of the medical coil of FIG. 15 after embolization of the tubing by formation of the embolic hydrogel indicated by the line.
Figure 17:
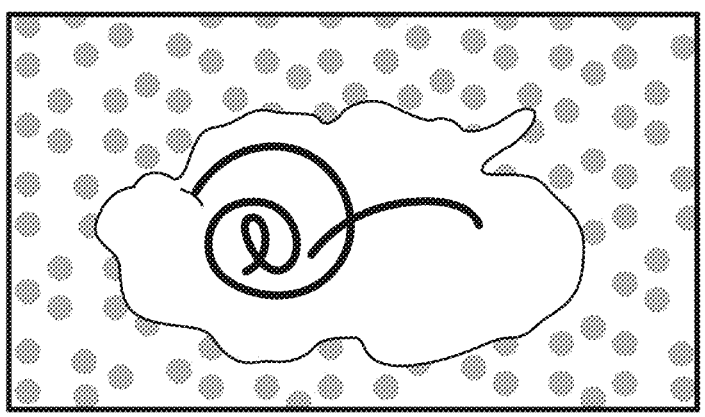
FIG. 17 is a photograph of the medical coil of FIG. 16 after it has been removed from the tubing.

A coil (VORTX 6 mm×6.7 mm, Boston Scientific, Minneapolis) was placed in the tube at the area of interest as depicted in FIG. 15, and five puffs of embolic components were released over about a minute. The embolic material was observed to form in contact with the coil but not at other locations, FIG. 16. The tubing was embolized and flow was stopped by the embolic material. The embolic material was removed and observed to be a tough, cohesive mass formed around the coil, FIG. 17.

Further Disclosure

1. An embolization system for controlling solidification in vivo of an embolic composition, comprising
   a first fluid supply containing a first liquid,
   a second fluid supply containing a second liquid,
   a water soluble polymer that comprises at least two functional groups that comprise an unsaturated hydrocarbon,
   an initiator, and
   a co-initiator,
   with the initiator being disposed in one of the first liquid and the second liquid and the co-initiator being disposed in the other of the first liquid and the second liquid,
   with the water soluble polymer being disposed in at least one of the first liquid and the second liquid,
   wherein a mixture of the first liquid and the second liquid provides for reaction of the initiator and the co-initiator to form a radical initiator for a free radical polymerization of the functional groups to covalently crosslink the water soluble polymer to form an embolization material.
2. The embolization system of 1 wherein a predetermined percentage of a dilution of a mixture of the first liquid and the second liquid prevents formation of the embolization material in less than 120 seconds as measured by in an in vitro gel time test. For instance, wherein the predetermined percentage of a dilution is in a range from 100% to 400%.
3. The embolization system of any of 1-2 wherein a 1:1 mixture of the first liquid and the second liquid forms the embolization material in no more than 5 seconds as measured by the in vitro gel time test.
4. The embolization system of any of 1-3 wherein the functional groups comprise one or more of an acrylate functional group or a methacrylate functional group.
5. The embolization system of any of 1-4 wherein a molecular weight, Mn, between the vinylic groups is at least 4000 Daltons.
6. The embolization system of any of 1-5 wherein the co-initiator comprises iron and is present at a concentration in a range from 0.2 to 200 mM.
7. The embolization system of any of 1-6 wherein the initiator is a peroxide, e.g., tert-butyl peroxide (TBHP).
8. The embolization system of 7 wherein a concentration of the peroxide is in a range from 10 to 10,000 parts per million (ppm).
9. The embolization system of any of 1-7 wherein the embolization material is a hydrogel.
10. The embolization system of 9 wherein a calculated distance between crosslinks of the hydrogel is at least 4000 Daltons, Mn.
11. The embolization system of 9 or 10 wherein a 1:1 mixture of the first liquid and the second liquid forms the embolization material that is a hydrogel that has a compression modulus from 1500-100,000 Pa.
12. The embolization system of any of 9-11 wherein a 1:1 mixture of the first liquid and the second liquid forms the embolization material that is a hydrogel that, at the time of formation, has a swellability of 20%-300% w/w.
13. The embolization system of any of 1-12 wherein the embolization material is cohesive.
14. The embolization system of any of 1-13 wherein the first liquid or the second liquid further comprises a co-initiator such as a reductant, provided that the reductant is not present in the same fluid supply as the initiator.
15. The embolization system of 14 wherein the reductant (co-initiator) comprises $Fe^{2+}$, $Cr^{2+}$, $V^{2+}$, $Ti^{3+}$, $Co^{2+}$, or $Cu^{+}$.
16. The embolization system of 14 or 15 wherein the reductant is provided as a salt chosen from the group consisting of an iron salt, ferrous sulfate, ferrous lactate, ferrous gluconate, and copper salt.
17. The embolization system of any of 14-16 wherein the reductant has a concentration in a 1:1 v/v mixture of the first liquid and the second liquid from 0.2-200 mM.
18. The system of any of 1-17 wherein the initiator comprises a peroxide group, an alkyl hydrogen peroxide group, or a persulfate.
19. The embolization system of any of 1-18 wherein a concentration of the initiator is from 50 to 10,000 parts per million (ppm).
20. The embolization system of any of 1-19 wherein the water soluble polymer comprises a polysaccharide, hyaluronic acid, a protein, a peptide, a polyethylene glycol (PEG), or a polyvinyl alcohol.
21. The embolization system of any of 1-20 wherein the water soluble polymer comprises at least 80% w/w (Mn) PEG.
22. The embolization system of any of 1-21 wherein a molecular weight of the water soluble polymer ranges from 4000 to 200,000 Daltons, Mn.
23. The embolization system of any of 1-22 wherein the water soluble polymer comprises a number of functional groups from 2-16.
24. The embolization system of any of 1-23 wherein the functional groups are independently chosen to comprise an unsaturated hydrocarbon, an acrylate functional group or a methacrylate functional group.
25. The embolization system of any of 1-24 further comprising a further water soluble polymer and/or a further precursor disposed in the first and/or second liquid.
26. The embolization system of 25 wherein the further water soluble polymer and/or further precursor comprises a plurality of functional groups.
27. The embolization system of any of 1-25 wherein a concentration of the water soluble polymer in the first liquid is from 5-50% w/w.
28. The embolization system of any of 1-27 wherein the first liquid and/or second liquid comprises a radiopaque contrast medium.
29. The embolization system of 28 wherein the radiopaque contrast medium comprises an iodo group, iopamidol, a triiodogroup, sodium diatrizoate, tungsten, or tantalum.

30. The embolization system of any of 1-29 wherein the first liquid and the second liquid are independently selected to have a viscosity suitable for passage through the catheter lumens.

31. The embolization system of any of 1-30 wherein the first liquid and the second liquid are aqueous liquids.

32. The embolization system of any of 1-31 wherein the embolization material is formed and effectively embolizes a vascular lumen when diluted by no more than 100%-250% v/v.

33. The embolization system of any of 1-32 wherein the embolization material is formed within 5 seconds as measured by a gel time test when the components are diluted by 0-100% v/v.

34. The embolization system of any of 1-33 further comprising a first flow metering control for the first liquid and a second flow metering control for the second liquid.

35. The embolization system of 34 wherein the first flow metering control and the second flow metering control are independently selected from the group consisting of a pump, syringe pump, and a peristaltic pump.

36. The embolization system of any of 34-35 wherein the first flow metering control and/or the second flow metering control are adjustable to change a rate of flow while delivering the first liquid and/or second liquid. Further, the adjustment may be made independently.

37. The embolization system of any of 34-35 wherein the first flow metering control and/or the second flow metering control are adjustable to change a rate of flow before delivery of the first liquid and/or second liquid.

38. The embolization system of any of 1-37 wherein the embolization system provides the first liquid and/or the second liquid in a range from 0.01 to 10 ml/second.

39. The embolization system of any of 1-38 wherein the water soluble polymer comprises polyethylene glycol, and the initiator comprises a peroxide, with the embolization system further comprising a reductant (co-initiator) disposed in the first liquid or the second liquid provided that the reductant is not in the same fluid supply as the peroxide, wherein the reductant is chosen from the group consisting of Fe2+, Cr2+, V2+, Ti3+, Co2+, and Cu+.

40. The embolization system of 39 wherein the reductant is Fe2+ and is provided by ferrous gluconate.

41. The embolization system of any of 1-40 further including a catheter comprising at least the first catheter lumen.

42. The embolization system of any of 1-41 wherein the catheter adaptor is a coaxial catheter adaptor connectable to
an inner catheter that has an outer diameter ranging from 0.005 to 0.1 inches,
an outer catheter having an inner diameter ranging from 0.01 to 0.2 inches,
with the inner catheter outer diameter being selected to pass through the outer tube lumen.

43. The embolization system any of 1-41 further comprising a catheter wherein a distal tip of the first catheter lumen is displaceable distally to the distal tip of the second catheter lumen by a distance adjustable from more than 0 mm to no more than 200 mm.

44. The embolization system of any of 1-43 wherein the catheter adaptor is a coaxial catheter adaptor, with the embolization system further comprising an inner catheter and an outer catheter connectable to the coaxial catheter adapter wherein a lumen of the inner catheter and a lumen of the outer catheter are independently selected to range from 0.005 to 0.2 inches diameter.

45. The embolization system of any of 1-44 being a kit.

46. A method of embolization comprising
delivering a first liquid comprising an initiator through a first catheter lumen to a target lumen and delivering a second liquid that comprises a co-initiator through a second catheter lumen to the target lumen, with at least one of the first liquid and the second liquid comprising a water soluble polymer that comprises a plurality of functional groups,
wherein the initiator and the co-initiator react with each other to form a radical initiator that initiates a free radical polymerization of the water soluble polymer functional groups to crosslink the water soluble polymer to form an embolization material in the target lumen when the first liquid and the second liquid mix with each other.

47. A method of embolizing a hypervascular tumor comprising
delivering a first liquid comprising an initiator through a first catheter lumen to a hypervascular tumor and delivering a second liquid that comprises a co-initiator through a second catheter lumen to the hypervascular tumor, with at least one of the first liquid and the second liquid comprising a water soluble polymer that comprises a plurality of functional groups,
wherein the initiator and the co-initiator react with each other to form a radical initiator that initiates a free radical polymerization of the water soluble polymer functional groups to crosslink the water soluble polymer to form an embolization material in the hypervascular tumor when the first liquid and the second liquid mix with each other.

48. A method of embolizing a vascular laceration comprising
delivering a first liquid comprising an initiator through a first catheter lumen to a vascular laceration and delivering a second liquid that comprises a co-initiator through a second catheter lumen to the hypervascular tumor, with at least one of the first liquid and the second liquid comprising a water soluble polymer that comprises a plurality of functional groups,
wherein the initiator and the co-initiator react with each other to form a radical initiator that initiates a free radical polymerization of the water soluble polymer functional groups to crosslink the water soluble polymer to form an embolization material in the vascular laceration when the first liquid and the second liquid mix with each other.

49. The method of any of 46-48 wherein a predetermined percentage of a dilution of a mixture of the first liquid and the second liquid prevents formation of the embolization material or provides a substantial delay in gel formation as measured by (a) a failure to form the embolization material in an in vitro gel time test or (b) a failure to form the embolization material in less than 120 seconds as measured by in an in vitro gel time test.

49. The method of any of 46-48 wherein the predetermined percentage of a dilution is in a range from 100% to 400% % v/v dilution of a 1:1 v/v mixture of the first liquid and the second liquid, e.g., 300%.

50. The method of any of 46-49 wherein a first catheter comprises the first lumen and a second catheter comprises the second lumen, with the first catheter and the second catheter being coaxially deployed.

51. The method of 50 wherein
the first catheter is an outer catheter and the second catheter is an inner catheter or
the first catheter is an inner catheter and the second catheter is an outer catheter.

52. The method of 51 wherein the inner catheter is slidably displaceable relative to the outer catheter to provide an offset distance between a distal tip of the inner catheter and the outer catheter.

53. The method of 52 further comprising displacing the distal tip of the inner catheter distal to the distal tip of the outer catheter.
54 The method of 53 wherein the first liquid and the second liquid are delivered with the distal tip of the inner catheter distal to the distal tip of the outer catheter.
55. The method of any of 46-54 wherein a 1:1 mixture of the first liquid and the second liquid forms the embolization material in no more than 5 seconds as measured by the in vitro gel time test.
56. The method of any of 46-55 wherein a 1:1 mixture of the first liquid and the second liquid forms the embolization material in no more than 5 seconds in vivo as measured by a cessation of flow visualized by subtraction angiography.
57. The method of any of 46-56 wherein the functional groups comprise an acrylate group and/or a methacrylate group.
58. The method of any of 46-57 wherein a molecular weight between the functional groups is at least 4000 Daltons.
59. The method of any of 46-58 wherein the first liquid comprises from 0.2 to 200 mM molar concentration of a reductant or iron.
60. The method of any of 46-59 wherein the initiator comprises a peroxide e.g., tert-butyl peroxide (TBHP).
61. The method of any of 46-60 wherein a concentration of the peroxide in the first liquid is from 10 to 3000 parts per million (ppm).
62. The method of any of 46-61 wherein the embolization material comprises a hydrogel.
63. The method of 62 wherein a calculated distance between crosslinks of the hydrogel is at least 4000 Daltons.
64. The method of any of 46-63 wherein a 1:1 mixture of the first liquid and the second liquid forms the embolization material that is a hydrogel that has a compression modulus from 1500-100,000 Pa.
65. The method of any of any of 46-64 wherein a 1:1 mixture of the first liquid and the second liquid forms the embolization material that is a hydrogel that, at the time of formation, has a swellability of 20%-300% w/w.
66. The method of any of 46-65 wherein the embolization material is cohesive.
67. The method of any of 46-66 wherein the embolization material does not adhere to tissue, such as the tissue that exposed to the embolization material, e.g., lumen walls, blood vessel.
68. The method of any of 46-67 wherein the co-initiator comprises a reductant.
69. The method of 68 wherein the reductant comprises $Fe^{2+}$, $Cr^{2+}$, $V^{2+}$, $Ti^{3+}$, $Co^{2+}$, or $Cu^{+}$.
70. The method of 68 or 69 wherein the reductant is provided as a salt chosen from the group consisting of an iron salt, ferrous sulfate, ferrous lactate, ferrous gluconate, and copper salt.
71. The method of any of 68-70 wherein the reductant has a concentration in a 1:1 v/v mixture of the first liquid and the second liquid from 0.2 to 200 mM.
72. The method of any of 68-71 wherein the initiator comprises a peroxide group, an alkyl hydrogen peroxide group, or a persulfate.
73. The method of any of 46-72 wherein a concentration of the initiator is from 50 to 5,000 parts per million (ppm).
74. The method of any of 46-73 wherein the water soluble polymer comprises a polysaccharide, hyaluronic acid, a protein, a peptide, a polyethylene glycol (PEG), or a polyvinyl alcohol.
75. The method of any of 46-74 wherein the water soluble polymer comprises at least 80% w/w (Mn) PEG.
76. The method of any of 46-75 wherein a molecular weight of the water soluble polymer ranges from 4000 to 200,000 Daltons, Mn.
77. The method of any of 46-76 wherein the water soluble polymer comprises a number of functional groups from 2-16.
78. The method of any of 46-77 wherein the functional groups are independently chosen to comprise an acrylate group or a methacrylate group.
79. The method of any of 46-78 further comprising a further water soluble polymer and/or a further precursor disposed in the first and/or second liquid.
80. The method of 79 wherein the further water soluble polymer and/or further precursor comprises a plurality of functional, e.g., unsaturated hydrocarbon or vinylic groups.
81. The method of any of 46-80 wherein a concentration of the water soluble polymer in the first liquid and/or the second liquid is from 5-50% w/w.
82. The method of any of 46-81 wherein the first liquid and/or second liquid comprises a radiopaque contrast medium.
83. The method of 82 wherein the radiopaque contrast medium comprises iopamidol, a triiodogroup, an iodo group, sodium diatrizoate, tungsten, or tantalum.
84. The method of any of 46-83 wherein the first liquid and the second liquid are independently selected to have a viscosity suitable for passage through the catheter lumens.
85. The method of any of 46-84 wherein the first liquid and the second liquid are aqueous liquids.
86. The method of any of 46-85 wherein the embolization material is formed and effectively embolizes a vascular lumen when diluted by no more than 100%-250% v/v.
87. The method of any of 46-86 wherein the embolization material is formed within 5 seconds as measured by a gel time test when the components are diluted by 0-100% v/v.
88. The method of any of 46-87 further comprising a first flow metering control for the first liquid and a second flow metering control for the second liquid.
89. The method of 88 wherein the first flow metering control and the second flow metering control are independently selected from the group consisting of a pump, syringe pump, and a peristaltic pump.
90. The method of any of 88-89 wherein the first flow metering control and/or the second flow metering control are adjustable to change a rate of flow while delivering the first liquid and/or second liquid. Further, the adjustment may be made independently.
91. The method of any of 88-90 wherein the first flow metering control and/or the second flow metering control are adjustable to change a rate of flow before delivery of the first liquid and/or second liquid.
92. The method of any of 46-91 wherein the method provides the first liquid and/or the second liquid at a rate that is in a range from 0.01 to 10 ml/second.
93. The method of any of 46-92 wherein the water soluble polymer comprises polyethylene glycol, and the initiator comprises a peroxide, and the co-initiator is chosen from the group consisting of $Fe^{2+}$, $Cr^{2+}$, $V^{2+}$, $Ti^{3+}$, $Co^{2+}$, and $Cu^{+}$.
94. The method of 93 wherein the co-initiator is $Fe^{2+}$ and is provided by ferrous gluconate.
95. The method of any of 46-94 further including a catheter comprising at least the first catheter lumen.
96. The method of any of 46-95 wherein the first catheter lumen is disposed in a first catheter and the second catheter lumen is disposed in a second catheter, with the first catheter and the second catheter being disposed side-by-side or coaxially.

97. The method of 93 with the first catheter and the second catheter being coaxial with one of the first and the second catheters being an inner catheter and the other of the first and the second catheters being an outer catheter, wherein the inner catheter has an outer diameter ranging from 0.005 to 0.1 inches, and the outer catheter has an inner diameter ranging from 0.01 to 0.2 inches, with the inner catheter outer diameter being selected to pass through the outer catheter lumen.

98. The method any of 46-97 comprising a catheter wherein a distal tip of the first catheter lumen is displaceable distally to the distal tip of the second catheter lumen by a distance adjustable from more than 0 mm to no more than 200 mm.

99. The method of any of 46-98 comprising connecting an inner catheter and an outer catheter to the coaxial catheter adapter wherein a lumen of the inner catheter and a lumen of the outer catheter are independently selected to range from 0.005 to 0.2 inches diameter.

100. The method of any of 46-99 wherein the target lumen is a blood vessel and comprising forming the embolization material in a plurality of vascular branches including embolization of one or more branches that have a diameter of less than 20 μm.

101. The method of any of 46-100 comprising delivery of the first liquid and/or second liquid in a series of partial doses separated by a period of time.

102. The method of any of 46-101 wherein the delivery of the partial doses is performed with real-time imaging.

103. The method of any of 46-102 wherein the total dose ranges from 0.5-50 ml.

104. The method of any of 46-103 being performed to treat a vascular laceration or a hypervascular tumor.

105. The method of any of 46-104 for treatment of a disease or pathological condition of a tissue, e.g., a blood vessel, organ, tumor, fibroid, cell mass, aneurysm, cancer, tumor, hypervascular tumor (cancerous or benign), aneurysm, aortic aneurysm, abdominal aortic aneurysm, peripheral aneurysm, hemostasis, vascular laceration, venous laceration, or tissue having a pathological condition.

106. The method of any of 46-105 wherein the target lumen is a blood vessel and comprising introducing the first fluid and the second fluid in a presence of flowing blood, with the first embolic component and the second embolic component forming the embolization material.

107. The method of any of 46-105 wherein the target lumen is an artery, vein, or aneurysm.

108. The method of any of 46-107 further comprising introducing a medical device at the target lumen.

109. The method of 108 where the medical device comprises one or more of: a coil, plug, hemostatic coil, hemostatic plug, bead, stent, filter, or balloon.

110. The method of any of 108-110 comprising releasing embolic components upstream of the medical device, with the embolic material being formed at the medical device.

111. A catheter system for controlling solidification in vivo of embolic compositions comprising:
an inner catheter,
a coaxial catheter adaptor providing a seal for sealing between the inner catheter and a coaxial outer catheter, with the adaptor providing an annular connector for fluid communication with an annulus between the inner catheter and a coaxial outer catheter,
an inner catheter fluid supply connectable to the inner catheter to provide fluid communication of a fluid with the inner catheter,
an outer catheter fluid supply connectable to the annular connector to provide fluid communication of a fluid with the annulus,
an initiator in a first liquid, and
a co-initiator in a second liquid,
and a water soluble precursor disposed in the first liquid and/or the second liquid,
wherein
the first liquid is disposed in the inner catheter supply and the second liquid is disposed in the outer catheter supply, or
the first liquid is disposed in the outer catheter supply and the second liquid is disposed in the inner catheter supply,
wherein mixing of the first liquid and the second liquid provides free radical polymerization of the functional groups to covalently crosslink the precursor to form an embolization material, wherein the first liquid and the second liquid are dilutable to prevent formation of the embolization material as measured by a failure to form the material within a predetermined time range when a 1:1 v/v mixture of the first liquid and the second liquid is diluted by, e.g., a 400% v/v dilution. Embodiments include a predetermined time in a range from 20 seconds to 5 minutes.

112. An embolization system for solidification in vivo of embolic compositions comprising:
a first fluid supply containing a first liquid at a first pH that comprises a precursor comprising a plurality of electrophilic functional groups and a precursor that comprises a plurality of nucleophilic functional groups,
a second fluid supply containing a second liquid that, when mixed at a 1:1 v/v ratio with the first liquid, causes the mixture of the first fluid and the second fluid to have a second pH favorable for reaction of the electrophilic functional groups with the nucleophilic functional groups,
a catheter adaptor connectable to the first fluid supply for delivery of the first liquid to a first catheter lumen and connectable to the second fluid supply for delivery of the second liquid to a second catheter lumen,
wherein a 1:1 v/v mixture of the first liquid and the second liquid provides for the electrophilic groups and the nucleophilic functional groups to react with each other to covalently crosslink the precursors to form an embolization material,
wherein a predetermined dilution of the mixture of the first liquid and the second liquid prevents formation of the embolic material or prevents formation of the embolic material for a predetermined time.

113. The embolization system of 112 wherein a dilution chosen from a range of 100%-400% v/v dilution of a 1:1 v/v mixture of the first liquid and the second liquid prevents formation of the embolization material as measured by a failure to form the embolization material within a predetermined time chosen from a range of 20 to 600 seconds in an in vitro gel time test.

114. The embolization system of 112 wherein the first and the second fluids provide a stoichiometric ratio ranging from 0.8:1 to 1.2:1 for the electrophilic groups to the nucleophilic groups when the first and the second liquids are mixed 1:1 v/v.

115. The embolization system of any of 112-114 wherein the nucleophilic functional groups are amine groups and/or primary amine groups and/or thiol groups and/or primary thiol groups.

116. The embolization system of any of 112-115 wherein the electrophilic functional groups are independently chosen from succinimide, succinimidyl esters, N-hydroxysuccimide groups, N-hydroxysuccimide ester groups, sulfosuccinimide groups, sulfosuccinimide ester groups N-hydroxysulfosuccinimide ester groups, N-hydroxyethoxylated succinimide ester groups, N-hydroxysuccinimidyl glutarate (SG), N-hydroxysuccinimidyl succinate (SS), N-hydroxysuccinimidyl carbonate (SC), N-hydroxysuccinimidyl adipate (SAP), and N-hydroxysuccinimidyl azelate (SAZ).

117. The embolization system of any of 112-116 wherein the first and second precursors are independently selected to comprises a polymer, a water soluble polymer, a polysaccharide, a protein, a peptide, a polyethylene glycol, or a polyvinyl alcohol.

118. The embolization system of any of 112-117 wherein the first and/or second precursor comprises at least 80% w/w (Mn) PEG.

119. The embolization system of any of 112-118 wherein a molecular weight of the first and the second precursor ranges from 200 to 500,000 Daltons, Mn.

120. The embolization system of any of 112-119 wherein a molecular weight of the precursor ranges from 200-2000 Daltons (Mn) and a molecular weight of the second precursor ranges from 10,000 to 300,000 Daltons (Mn).

121. The embolization system of any of 112-120 wherein the first and the second precursors are independently chosen to comprise a number of functional groups from 2-200.

122. The embolization system or methods of any of 1-112 further comprising an aqueous solution for use in the first and/or the second liquid, with the solution being in a pharmaceutically acceptable form, meaning highly purified and free of contaminants, e.g., pyrogens. For instance, as provided in a kit.

123. A method of forming an embolic material at a medical device at a vascular location comprising
introducing a catheter into a vascular lumen at a position wherein blood in the vascular lumen flows in a direction from the catheter towards the medical device at the vascular location;
releasing a plurality of embolic components from the catheter into the vascular lumen, wherein the embolic components chemically react with each other to form an embolic at the medical device.

124. The method of 123 wherein the embolic material is formed in contact with the medical device. Examples of the medical device are: coils, plugs, hemostatic coils, hemostatic plugs, beads, stent, filters, balloons. The method may include placement of the medical device at the vascular location.

125. A method of forming an embolic material at a vascular location comprising
introducing a catheter into a vascular lumen at a position wherein blood in the vascular lumen flows in a direction from the catheter towards the vascular location;
restricting a flow of blood around the catheter,
releasing a plurality of embolic components from the catheter into the vascular lumen, wherein the embolic components chemically react with each other to form an embolic material at the vascular location.

126. The method of 125 wherein the embolic material is formed only when restricting the flow of blood around the catheter.

127. The method of 125 or 126 wherein restricting a flow of blood around the catheter comprises inflating a balloon, e.g., a balloon located on a distal portion of the catheter.

128. The method of any of 125-127 wherein restricting a flow of blood around the catheter comprises stopping blood flow or reducing the blood flow without stopping the blood flow.

129. The method of any of 123-128 wherein the plurality of embolic components comprises one or more embolic components described hereinabove, e.g., as enumerated in any of 1-119.

130. The method of any of 123-129 wherein the plurality of embolic components comprise a first embolic component comprising a precursor having a vinylic group and a second embolic component comprising an initiator.

131. The method of any of 125-129 wherein the plurality of embolic components comprise a first embolic component comprising a precursor having an electrophilic functional group and a second embolic component comprising a nucleophilic functional group.

132. The method of any of 123-131 wherein the catheter is a multilumen catheter, e.g., a coaxial catheter.

133. A system or kit comprising one or more components used in the methods of any of 123-132.

134. A use of the embolization system or methods of any of 1-133 for treatment of a disease or pathological condition of a tissue, e.g., a blood vessel, organ, tumor, fibroid, cell mass, cancer, tumor, hypervascular tumor (cancerous or benign), aneurysm, aortic aneurysm, abdominal aortic aneurysm, peripheral aneurysm, hemostasis, vascular laceration, venous laceration, or tissue having a pathological condition.

135. A method of treating a disease or pathological condition of a tissue comprising administering, to a mammal, an amount of embolization components effective to embolize the tissue, the embolization components being as set for at any of 1-132 or as further provided herein.

136. The method of 135 wherein the tissue is one or more of: a blood vessel, organ, tumor, fibroid, cell mass, cancer, tumor, hypervascular tumor (cancerous or benign), aneurysm, aortic aneurysm, abdominal aortic aneurysm, peripheral aneurysm, hemostasis, vascular laceration, venous laceration, or tissue having a pathological condition.

It is claimed:

1. A method of embolization comprising
delivering a first liquid comprising an initiator through a first catheter lumen to a target lumen and delivering a second liquid that comprises a co-initiator through a second catheter lumen to the target lumen, with at least one of the first liquid and the second liquid comprising a water soluble polymer that comprises at least 80% by weight, based on the total weight of the water soluble polymer, of polyethylene glycol having a plurality of functional groups that form radical initiated crosslinks, wherein the initiator and the co-initiator react with each other to form a radical initiator that initiates a free radical polymerization of the water soluble polymer functional groups to crosslink the water soluble polymer to form an embolization material in the target lumen when the first liquid and the second liquid mix with each other wherein the crosslinked polymer is a hydrogel with a swelling of about 20% or greater.

2. The method of claim 1 wherein a dilution in a range from 100% to 400% v/v dilution of a 1:1 v/v mixture of the first liquid and the second liquid prevents formation of the embolization material for at least 120 seconds as measured by an in vitro gel time test.

3. The method of claim 2 wherein the functional groups comprise an acrylate group and/or a methacrylate group.

4. The method of claim 3 wherein the 1:1 v/v mixture of the first liquid and the second liquid forms the embolization material in no more than 5 seconds as measured by the in vitro gel time test.

5. The method of claim 4 wherein the initiator comprises a peroxide.

6. The method of claim 5 wherein a concentration of the peroxide in the first liquid is from 10 to 3000 parts per million (ppm).

7. The method of claim 6 wherein the co-initiator comprises a reductant.

8. The method of claim 7 wherein the reductant comprises $Fe^{2+}$, $Cr^{2+}$, $V^{2+}$, $Ti^{3+}$, $Co^{2+}$, or $Cu^{+}$.

9. The method of claim 8 wherein a concentration of the reductant in the 1:1 v/v mixture of the first liquid and the second liquid is from 0.2 to 200 mM.

10. The method of claim 1 wherein the water soluble polymer comprises a number of vinylic groups in a range from 2 to 16 and wherein a calculated spacing between crosslinks of the hydrogel is from 4000 Daltons to 200,000 Daltons.

11. The method of claim 1 wherein the water soluble polymer further comprises hyaluronic acid, a protein, a peptide, or a polyvinyl alcohol.

12. The method of claim 1 wherein the first liquid and/or second liquid comprises a radiopaque contrast medium.

13. The method of claim 1 wherein the embolization material is a cohesive hydrogel.

14. The method of claim 1 wherein the first catheter lumen is coaxially deployed within the second catheter lumen.

15. The method of claim 14 wherein the first liquid and the second liquid are delivered with the distal tip of the inner catheter distal to a distal tip of the outer catheter.

16. The method of claim 1 wherein the embolization material is formed in a hypervascular tumor, a vascular laceration, a blood vessel, an organ, a tumor, a fibroid, a cell mass, an aneurysm, an aortic aneurysm, abdominal aortic aneurysm, a peripheral aneurysm, for hemostasis, a venous laceration, or a tissue having a pathological condition.

17. The method of claim 15 wherein a distal tip of the first catheter lumen is located distally relative to a distal tip of the second catheter lumen by at least 2 mm.

* * * * *